US009079268B2

(12) United States Patent
Fry et al.

(10) Patent No.: US 9,079,268 B2
(45) Date of Patent: Jul. 14, 2015

(54) ANALYTICAL LASER ABLATION OF SOLID SAMPLES FOR ICP, ICP-MS, AND FAG-MS ANALYSIS

(71) Applicants: Robert C. Fry, Omaha, NE (US); Steven K. Hughes, Longmont, CO (US); Madeline J. Arnold, Lincoln, NE (US)

(72) Inventors: Robert C. Fry, Omaha, NE (US); Steven K. Hughes, Longmont, CO (US); Madeline J. Arnold, Lincoln, NE (US)

( * ) Notice: Subject to any disclaimer, the term of this patent is extended or adjusted under 35 U.S.C. 154(b) by 354 days.

(21) Appl. No.: 13/573,554

(22) Filed: Sep. 24, 2012

(65) Prior Publication Data

US 2015/0165550 A1 Jun. 18, 2015

Related U.S. Application Data

(63) Continuation-in-part of application No. 12/283,698, filed on Sep. 14, 2008, now Pat. No. 8,274,735.

(60) Provisional application No. 60/993,795, filed on Sep. 14, 2007, provisional application No. 61/134,136, filed on Jul. 7, 2008.

(51) Int. Cl.
*G02B 21/26* (2006.01)
*B23K 26/03* (2006.01)
*G01N 21/71* (2006.01)
*G02B 5/08* (2006.01)
*B23K 26/14* (2014.01)

(52) U.S. Cl.
CPC .......... *B23K 26/032* (2013.01); *B23K 26/1405* (2013.01); *G01N 21/71* (2013.01); *G02B 5/0891* (2013.01); *G01N 2201/06113* (2013.01)

(58) Field of Classification Search
USPC ........................ 359/393, 398; 356/51, 72, 318
See application file for complete search history.

(56) References Cited

U.S. PATENT DOCUMENTS

| | | | |
|---|---|---|---|
| 4,685,648 A | 8/1987 | Dobner et al. | 248/572 |
| 5,313,043 A * | 5/1994 | Yamagishi | 219/121.68 |
| 5,774,240 A | 6/1998 | Goto et al. | 359/12 |
| 6,586,258 B1 | 7/2003 | Bair et al. | 436/174 |
| 2006/0252047 A1 | 11/2006 | Ekstrom et al. | 435/6 |
| 2008/0198373 A1 | 8/2008 | Kosmowski et al. | 356/244 |

OTHER PUBLICATIONS

"Entrainment and Transport of Laser Ablated Plumes for Subsequent Elemental Analysis", Peter Arrowsmith and Steven Hughes, Applied Spectroscopy, vol. 42, No. 7, 1988, pp. 1231-1239.*
"Laser Ablation for Direct ICP and ICP-MS Analysis", Gases & Instrumentation, Jul./Aug. 2008, vol. 2, issue 4, pp. 1-5.*

* cited by examiner

*Primary Examiner* — Frank Font
(74) *Attorney, Agent, or Firm* — James D. Welch

(57) ABSTRACT

This invention is improved laser ablation of solid samples analyzed by inductively coupled plasma (ICP), ICP mass spectrometry, or flowing afterglow mass spectrometry. A mirror-with-hole eliminates chromatic aberration in sample viewing and allows rad-hardening for radiation hot cell analysis of nuclear waste. Other attributes facilitate comprehensively rad-hardened laser ablation. Additional improvements include large, homogeneous laser spots, long-focus objective lenses, variable laser path length with built-in re-alignment, variable demagnification ratio, higher powered SMR lasers with larger spots enabling sensitive bulk solids analysis, demountable gravitationally self sealing stack assembly sample ablation cells, and laser ablation sample changers.

20 Claims, 26 Drawing Sheets

ANALYTICAL LASER ABLATION OF SOLID SAMPLES FOR ICP, ICP-MS, AND FAG-MS ANALYSIS

CROSS REFERENCE TO RELATED APPLICATIONS

This application is a C.I.P. of U.S. application Ser. No. 12/283,698, filed Sep. 14, 2008 (scheduled to issue Sep. 25, 2012 as U.S. Pat. No. 8,274,735) and therevia claims benefit of U.S. Provisional Application Ser. Nos. 60/993,795 and 61/134,136 filed on Sep. 14, 2007 and Jul. 7, 2008, respectively. Said application Ser. No. 12/283,698 and said U.S. Provisional Applications No. 60/993,795 and 61/134,136 are hereby incorporated by reference.

FIELD OF THE INVENTION

This invention relates to 1.) improved optical viewing of ultraviolet (hereafter "UV") laser ablation processes involving solid materials, and to 2.) high sensitivity analysis of solid materials by analytical UV laser ablation, and to 3.) large spot bulk analysis of solid materials by analytical UV laser ablation, and to 4.) automated (mechanized) sample changing for analytical laser ablation, and to 5.) laser micro-machining, and to 6.) large depth-of-focus laser ablation for ablating rough, uneven or non-level surfaces, and to 7.) wide-range, variable demagnification ratio laser ablation, and to 8.) rad-hardened analytical UV laser ablation for analysis of high activity solid nuclear waste (e.g. vitrified as radioactive glass) in a radiation "hot cell",
in which a focused UV laser beam removes (by optical ablation at focused laser energy densities (more precisely, irradiance) exceeding the surface damage threshold of said solid material) a portion from the surface of said solid materials, for purposes of altering the shape or topography of said solid materials, or for purposes of obtaining vapors, or smoke, or a particulate aerosol from a laser ablation event occurring on the surface of said solid material, or obtaining a mixture of vapors, smoke, and/or particulate aerosol from a laser ablation event occurring on the surface of said solid material, which vapors, smoke, or particulate aerosol, or which mixture of vapors, smoke, and/or particulate
aerosol may then be directed to an external analytical instrument (e.g. inductively coupled plasma (ICP) emission, ICP mass spectrometer (ICP-MS), or flowing after-glow (FAG) mass spectrometer (FAG-MS), said external analytical instrument being capable of providing chemical and/or elemental analysis of said vapors, or smoke, or particulate aerosol, or said mixture of vapors, smoke, and/or particulate aerosol, said chemical and/or elemental analysis being indicative and representative of the chemical or elemental content and/or composition of the original said solid sample materials.

The invention therefore relates to UV laser ablation micromachining (e.g. in an industrial setting), and/or to analytical UV laser ablation in a general solid sample analysis laboratory or a radiation "hot cell" environment,
and more specifically, the invention relates to 1.) improved optical viewing (by an observer or camera) of the solid material surface to be ablated, and/or during ablation, and/or post-ablation in UV laser ablation, via a reduction of chromatic aberration to allow an observer (or camera) to view (more clearly) the area to be ablated, to view (more clearly) the process of ablation, and/or view (more clearly) the result of ablation, in such a way as to allow an observer to better identify and/or pre-select the area to be ablated, to more clearly view and video-record the ablation event in order to assess ablation process characteristics, and/or to more clearly view the result of ablation on the solid material surface to assess ablation effectiveness and ablation crater or trench morphology and compare that with previous or future ablation experiments in same or other materials under same or varied ablation conditions, said observation being typically optically magnified and then viewed by direct human visual inspection through a magnified optical eyepiece, or a video-camera, or CCD array camera which may be used to capture and/or record images for immediate (real-time) display on a monitor screen, and/or for storage in a computer file,
and further, the invention specifically relates to 2.) high sensitivity analytical UV laser ablation, 3.) large spot bulk analysis in analytical UV laser ablation, and 4.) laser micro-machining, respectively in which substantially larger (than normal) invention UV lasers may be employed in an invention stable multimode resonator (SMR) lasing condition coupled with an invention external optical configuration for larger SMR lasers which results in an inherently homogenized near field invention laser beam profile being efficiently transferred without homogeneity loss to a far field sample surface, which results in external substantially larger invention material ablation rates in these three areas (enumerated above) without increasing the average particle size of smoke or aerosol resulting from the ablation, and creating a more homogeneous focused high powered laser spot capable of ablating more flat bottomed craters and trenches, without deteriorating the "quality" of ablation craters and/or trenches produced (in terms of crater (and/or trench) edge cut (sharp, clean edges without cracking, chipping, or shattering) and/or bottom shape (e.g. bottom flatness)),
and further, the invention specifically relates to 5.) exceptionally large depth-of-focus laser ablation in focusing a laser-light image of a laser illuminated aperture (hereafter laser spot) onto the surface of a target solid sample or target material for ablating rough, non-flat, non-parallel, non-level, or otherwise uneven target surfaces to facilitate tolerance of surface variations (from flat and level) as large as 1-2 mm for either stationary laser spot ablation or line scan ablation and/or raster pattern ablation without refocusing, re-leveling, or resurfacing (e.g. grinding flat) the target sample or material.
and further, the invention specifically relates to 6.) wide-range variable demagnification invention laser ablation, in which large changes in invention optical demagnification of the laser spot may be made on an operational basis in a single invention laser ablation system to optimize ablation rates, aerosol quality, and or crater and/or trench size and quality within the ideal irradiance range (IIR) of each material and for a wide variety of different solid materials,
and further, the invention specifically relates to 7.) automatic (mechanized) solid sample changing for analytical laser ablation,
and finally, the invention specifically relates to 8.) rad-hardened invention analytical laser ablation of solid sample materials in a radiation "hot cell" containing radioactive sample material such as nuclear waste, in which optical components (of the invention laser ablation system) that may otherwise be prone to radiation damage are eliminated from the invention design, or are located outside the hot cell (but in adjacent proximity to the hot cell), or are shielded within the hot cell, or are located within the hot cell at greater distance from radioactive material (and hence receive reduced radiation levels by the "inverse square" law).

BACKGROUND OF THE INVENTION

A description of laser ablation in the publication of Arrowsmith and Hughes, APPLIED SPECTROSCOPY, 42, 7, 1988

(1231-1239) is commonly cited as the beginning of modern analytical laser ablation for inductively coupled plasma (ICP) emission and inductively coupled plasma mass spectrometry (ICP-MS) analysis of solid samples. More recently, the July 2008 issue of Gases & Instruments features an article by Hughes, Brady, and Fry which reviews the use of UV lasers and analytical laser ablation in general, with illustration of how white light illumination and viewing is normally done for UV laser ablation and discussion of parameters affecting ablation quality, ablation morphology, ablation rate, and related aerosol particle size from an ablation event. From the G&I article it should be noted that an opto-mechanical (OM) ablation is desired for analytical laser ablation, rather than a thermal process. It should also be noted from the G&I article that a small particle size is desired in the aerosol resulting from an ablation event, to ensure efficient aerosol mass transport (to the external analytical instrument) and to minimize overall system calibration difficulty and variability.

FIGS. 1A, 1B illustrate that a dichroic mirror (6) is normally used in prior art analytical UV laser ablation, to allow a view camera (22) to view a solid material (11, 24) coaxially (18, 19, 20) with a final segment of the UV laser beam (7, 10, 24) which is also focused to ablate the surface of the solid material (11, 24). The prior art dichroic mirror (6) has a very thin film mirror coating which is highly reflective only to light of a specific UV laser wavelength, which is the specific "design" wavelength of the particular (dichroic) laser mirror in question, and which is based on selective constructive interference (in the reflection mode) of light at that design wavelength, exclusively. All other wavelengths (shorter and longer than the specific UV design wavelength) are not reflected. Instead, the thin mirror coating is transparent to the other wavelengths (e.g. visible light) and passes them like a window (even if angled). FIGS. 1A, 1B thereby illustrate that the prior art UV laser beam (5, 7) may be efficiently reflected from the angled side of an appropriately designed UV dichroic mirror (6) towards a solid sample surface (11, 24), while an overhead visible "white light" camera (20, 22) view may be taken through the same prior art angled UV dichroic laser mirror (6) from the top, since the UV dichroic laser mirror (6) is transparent to visible (e.g. "white") light.

The prior art objective lens (8) performs two functions. First it focuses the UV laser beam (7, 10) downward onto the solid sample material surface (24); second, it simultaneously operates (in reverse) to coaxially focus a visible, white light image of the solid sample surface (24) upward (18, 19, 20) to the camera (22) focal plane. (It should be noted that an auxiliary visible, white light source, e.g. ring illuminator (16) is typically also provided to coaxially illuminate (17) a relatively wide area (e.g. 1-10 mm) of the solid sample surface (11, 24) continuously (to light the "subject" for the camera view), while the pulsed, Q-switched UV laser fires (flashes) intermittently (10), but repetitively to ablate a smaller spot (24, e.g. 0.02-0.2 mm) on the solid sample surface.)

The disadvantage of the prior art coaxial camera view of laser ablation in FIGS. 1A, 1B is that both the laser beam (7, 10) and the camera view (18, 19, 20, 22) must pass through the same short focal length prior art objective lens (8), albeit in opposite directions, so the two prior art optical paths are (undesirably) coupled. The prior art objective lens (8) must be designed to efficiently pass (7, 10) UV laser radiation (e.g. 193 nm, 213 nm, and 266 nm) with high transparency at UV wavelengths. The available optical materials (for doing that) do not simultaneously allow an ideally achromatic focused visible (e.g. 400 nm-700 nm) "white light" view for the prior art camera path (18, 19, 20, 22). The prior art UV laser objective lens (8) can produce a good quality monochromatic UV laser image (24), but then it is not achromatic for longer wavelength visible light and therefore cannot focus both ends of the white light spectrum (red and blue) simultaneously in the same prior art camera plane (22). Undesirable chromatic aberration thus arises for the prior art "white light" on-axis view, in order to ensure a good UV laser ablation experiment. A poorly focused prior art "white light" (camera) image (22) therefore adversely affects many analytical UV laser ablation systems today, and there remains a need to decouple the visible white light camera view (22) from the chromatic aberration of a UV laser objective lens (8).

A second disadvantage of prior art UV analytical laser ablation is that low ablation rates and poor sensitivity for bulk solid analysis typically result under conditions where a high quality opto-mechanical (hereafter OM) ablation occurs with prior art UV analytical laser ablation systems. The basic problem arises from a situation where UV analytical laser ablation (for ICP and ICP-MS) is a relatively new field, with complete (integrated) prior art analytical systems becoming commercially available for the first time in 1995. With UV analytical laser ablation still in its "infancy" (a relatively small number of installations as of this writing), prior art commercial analytical laser ablation manufacturers are both small in size and few in number. Thus far (1995-present), the small group of prior art analytical laser ablation manufacturers have primarily been designing prior art products tailored to the needs of a narrowly focused group of customers working in Geology.

Geologists have certainly done the infant analytical laser ablation field a significant service by purchasing prior art commercial units early in its manufacturing development cycle, thereby making the infant field of analytical laser ablation commercially viable (albeit on a relatively small commercial scale). Through effective lobbying, they (geologists) have influenced the small group of prior art analytical laser ablation manufacturers and successfully imposed their own particular (geologic) biases onto the features and characteristics of commercially available prior art system configurations. The few existing prior art analytical laser ablation manufacturers have therefore catered primarily to the (prior art) geologic "configuration bias" (hereafter, "geo-bias"), rather than designing flexible, general purpose analytical laser ablation systems of the type that would be needed for widespread usage for bulk analysis of solid materials in general, for a wider variety of laboratories.

The prior art geo-bias typically dictates a small, homogeneous focused spot diameter, since geologists are typically interested in elemental analysis of small inclusions and other small heterogeneities in rocks and minerals. Consequently, focused laser spot diameters as small as 2 micron are desired in the geo-bias, and prior art excimer and SMR analytical UV laser ablation systems are not sold with a homogeneous focused spot diameter larger than 200 microns. Prior art SMR analytical UV laser ablation objective lenses (8, FIG. 1A-1B) to produce such small homogeneous spot diameters typically exhibit short focal length (e.g. F=18-38 mm) and their working distance (to the sample surface) is only slightly more than that. This prior art geo-bias for short focal length objective lenses and small spot diameters is ideal for geologists interested in analyzing small isolated features in heterogeneous rocks and minerals, but it is not ideal for high sensitivity bulk solids analysis or more homogeneous sample materials in other fields.

The short focal length objective lens and small spot diameters characteristic of the geo-bias in prior art SMR analytical laser ablation, actually preclude using high laser power to enhance sensitivity. In fact, there is a certain maximum laser power that can be optimally employed for prior art focused laser spots of 200 microns diameter and less, which is the largest homogeneous focused spot available in commercial prior art excimer and SMR analytical laser ablation systems. In prior art analytical laser ablation manufacturing, the geo-bias therefore leads to use of relatively small excimer and SMR UV lasers (less than 12 mJ at 266 nm) and short laser path lengths. This keeps the system size and price down, but it also limits the sensitivity which can be obtained in bulk solids analysis with a prior art system.

At ETH-Zurich, Guenther, Horn, and Guillong employed larger prior art Gaussian beam (TEM 00) lasers with external prior art beam homogenizing optics, and a large excimer laser was substituted in a commercial prior art system (Geo-Lase by Coherent, distributed for several years by CETAC), but in both cases, the external beam homogenizers were inefficient (subject to significant light transmission loss), the firing frequency reduced to 10 Hz maximum for the TEM 00 Nd-YAG laser, and the objective lenses were characterized by the short geo-bias focal length (F<40 mm) and relatively small maximum focused spot diameter in both cases, so the actual final output (relating to ablation rate) of these prior art systems was only slightly more than the smaller, more efficient, prior art frequency-multiplied SMR Nd-YAG analytical UV laser ablation systems, and sensitivity for bulk analysis wasn't appreciably enhanced with either of these two larger prior art lasers and their associated ablation systems.

One larger (40 mJ) prior art commercial Nd-YAG laser ablation system operating at 266 nm, 10 Hz was coupled to a maximum focused spot size of 780 μm (0.78 mm), but this prior art laser ablation system (MACRO by New Wave, Inc.) wasn't designed for operation in the SMR mode to produce a homogenized beam profile. It was instead an unstable multimode resonator (UMR) with a gradient reflectance mirror (GRM), by design. The prior art GRM unstable resonator is actually designed for small spot focusing (low divergence rate, compared to SMR) and it is well known that the GRM unstable multimode resonator (UMR) does not produce the desirable homogenized beam profile for large spots, and is instead characterized by a "donut with hole" or "scooped" beam profile. Initial laser ablation testing with this prior art GRM unstable resonator (UMR) analytical laser ablation system determined that it was not a reliable configuration at high power (40 mJ, 266 nm). This prior art unstable resonator (UMR) deteriorated rapidly in terms of power output and ablation crater quality. In summary, the GRM unstable multimode resonator (UMR) beam profile is not homogeneous like an SMR, and the limited prior art firing frequency of 10 Hz further reduces the sensitivity of a MACRO system relative to 20 Hz SMR system. Finally, the energy output of this unstable resonator has been reported to be erratic and frequently dropping to 20 mJ instead of the 40 mJ UMR rating.

There remains a need for high sensitivity analytical UV laser ablation based on a stable, reliable, high powered (e.g >12 mJ @ 266 nm, with similar higher powered 213 nm and 193 nm systems) homogenous beam SMR (stable multimode resonator) laser with a firing frequency higher than 10 Hz and a laser objective lens with focal length greater than F=40 mm with reduced demagnification to produce larger homogeneous focused spot diameters (>200 um) commensurate with higher laser power to achieve high analytical sensitivity within the ideal irradiance range (IIR) of solid sample materials.

The referenced G&I article indicated that each different solid sample material has a relatively narrow range of focused laser irradiance (joules/cm$^2$/ns) which is ideal for producing the best OM ablation characteristics. Operating within the ideal irradiance range (IIR) for a given material minimizes thermal ablation effects (which otherwise make calibration more difficult and unreliable) and yields the smallest aerosol particle size. If the focused laser ablation irradiance is lower than the IIR for a given material, then thermal ablation predominates, ablation rates are low, calibration is difficult and unreliable, and analytical sensitivity is poor. If the focused laser irradiance is higher that the IIR of a material, then that sample is "over powered" and undesirable sample shattering and cracking occurs, destabilizing the analytical instrument response without significantly improving the sensitivity. In this case, ablation is too violent (rough) and too many large particles are blown out of the ablation crater, the large particles being too large for efficient transport to the external instrument. They wind up splattered throughout the ablation cell, settling out on various cell and tubing wall surfaces without transporting to the plasma or contributing appreciably to the analysis. In such an overpowered situation, the signal in the external instrument becomes temporally unstable. The ideal irradiance range (IRR) should therefore be maintained for each material and should not be exceeded.

For small focused spot diameters (<200 um) characteristic of the geo-bias, the IIR is matched with relatively small, low powered SMR UV lasers and relatively short prior art laser paths and short focal length prior art objective lenses. For example, for a 266 nm ($4^{th}$ harmonic) pulsed, Q-switched, Nd-YAG laser, SMR systems in the range of 9-12 mJ are about the limit of useful laser size, in prior art commercial systems where the geo-bias prevails to limit the maximum focused prior art spot diameter to 200 microns or less. Larger lasers of 30 mJ, 40 mJ, 50 mJ, 60 mJ, 90 mJ, and 230 mJ are available at 266 nm and the desired SMR mode, but these have typically not been used for prior art analytical laser ablation, simply because the geo-bias prevailing in that industry precludes their usage in prior art short path applications with a focused spot size range 2-200 microns, where they would simply over-power the ideal irradiance range (IIR) of virtually all solid samples.

The overall result of favoring smaller lasers, shorter path lengths, and limited spot diameter (geo-bias in the prior art analytical laser ablation industry) is that prior art system sizes and prices are "contained", but analytical sensitivities in this prior art configuration are limited to the part-per-million (ppm) range for ICP and ICP-MS analysis of solids. There is no reported prior art high sensitivity (part-per-billion, ppb) analytical UV laser ablation system based on a stable multimode resonator (SRM) and which produces homogeneous focused spot diameters up to 1.5 mm (in a preferred embodiment) and allows use of pulsed SMR 266 nm lasers as large as 50 mJ-230 mJ in a long path length configuration, or other equivalently oversized UV lasers at even shorter wavelength, while still operating within the optimized IIR of solid materials.

An invention is therefore needed for analytical UV laser ablation in which the ppm (part-per-million) sensitivity limitations of the prior art short laser path, short objective focal length, high demagnification ratio and small spot geo-bias would be removed via replacement with a more sensitive analytical laser ablation invention employing longer laser path lengths and longer focal length objective lenses in a ratio favoring lower demagnification ratios and larger spot diameters from larger SMR lasers operating at full power, coupling most of their energy into the sample without exceeding IIR values of solid materials to be analyzed. This would enhance the sensitivity of bulk analysis by analytical laser ablation and lead to a new era of high sensitivity (ppb (part-per-billion)) bulk analysis in the solid phase. It would be further desirable if this were achieved simultaneously with the aforementioned invention decoupling of laser focusing from white light focusing.

Since the ideal irradiance range (IIR) varies widely in solid materials, but is a relatively narrow range for each material, it is apparent that conventional systems with fixed demagnification ratio have a limited ability to maintain the IIR of each material in a wide range of solid materials, while simultaneously running the system at 100% laser power and using the full laser beam to maximize ablation rates. If a larger laser were selected, optical attenuation or power attenuation could be employed to "throttle it back" and keep all samples within their respective IIR's, but if the demagnification ratio is fixed as with prior art systems, ablation rates will not be kept at the maximum possible ablation rate for that laser over a wide range of solid sample materials.

There remains a need for an invention which would allow wide range, operationally variable demagnification ratio (operationally variable maximum spot diameter), so that the laser may be operated at 100% power output while the ablation proceeds within the IIR of each solid material by simply having the spot diameter adjusted so that 100% of the laser power is delivered within the IIR of that material. This could theoretically be done to a limited extent with a turret holding 2 to 4 different interchangeable objective lenses to yield several different demagnification ratios, but the number and range of focal lengths which may be accommodated in a single turret (for a fixed turret-to-laser head "object" distance and a limited range of turret-to-sample image distance variation) is limited to about 3 or 4 lenses whose focal lengths are not widely varying (one from the other). The IIR of solid materials varies more widely than an objective lens turret could cover by itself. In order to accommodate a wider range of IIR, an invention with an operationally variable laser "object" distance (over wide range) and an operationally variable laser "image" distance (over wide range) is also needed (or needed instead). Essentially, there remains a need for a laser ablation system with operationally variable path (over a large range of path length) to create a larger range of demagnification ratios for each objective lens. Such an invention would benefit both analytical laser ablation and laser micromachining applications.

A third disadvantage of prior art analytical laser ablation is that the currently prevailing geo-bias involving relatively short prior art laser path lengths and short prior art laser objective focal lengths yields a shallow depth-of-focus (in the focused prior art laser spot) of only about 0.25 mm or less. If the sample surface roughness, topography, flatness, or deviation from parallel (to ablation cell horizontal translation axis when mounted in cell) varies by more than this, different locations on the sample surface must be refocused upon changing location in a prior art system. For a laser ablation line scan or raster pattern involving controlled (motorized, FIG. 1B, items 47-52) horizontal sample motion (during ablation), it is obvious that the sample flatness (and degree to which the sample surface is held parallel to the axis of motion) must be less than the depth-of-focus of the laser spot doing the ablation, otherwise the spot will lose focus and the ablation rate will change during the horizontal motion scan or raster on the sample surface. This typically means that the sample must be flat and parallel to the motion axis, within 0.25 mm (250 μm) or less in a prior art system, and it often requires that solid samples with surface roughness or uneven topography (greater than this) must be cut or ground flat, prior to ablation.

As one of the principal advantages of laser ablation (compared to acid dissolution of solid samples prior to ICP or ICP-MS analysis with nebulizer introduction of the resulting liquid) is supposed to be "elimination of sample preparation", the oft-required cutting, grinding, or pelletizing of irregular surfaced solid samples for conventional prior art laser ablation is clearly counter-productive. There remains a need for an analytical laser ablation invention with increased depth-of-focus (in the focused laser spot) from the current prior art range of 0.25 mm (or less) to a much larger invention depth-of-focus such as 1 mm or even 2 mm, to accommodate greater surface roughness and larger variation in surface topography for laser ablation analysis without prior sample preparation or resurfacing by cutting, grinding, or pelletizing.

A fourth disadvantage to prior art laser ablation is the lack of an automated sample changer, which (lack) prevents automated sequential analysis of a large group of samples, or even a small group of samples if they are too large for more than one of them to fit into the ablation cell at any one time. Many reasons preclude the use of an auto-sampler in prior art analytical laser ablation. For one example, the short focal length prior art objective lenses (geo-bias) typically do not allow room for the sample cell to be automatically opened while positioned under the objective lens. There remains a need for development of an automatic (mechanized) sample changer for analytical laser ablation.

A fifth disadvantage of prior art analytical laser ablation is that, in the field of high activity nuclear waste analysis, prior art analytical UV laser ablation has heretofore not been well suited to a radiation "hot cell" environment, due to rapid prior art laser ablation component failure upon exposure to high level radioactivity. Typical key conventional prior art laser ablation component failures occur within 500-1,000 rads total accumulated exposure. With high activity nuclear waste samples in a hot cell, exposure rates of 1,000-2,000 rads/hour are to be expected. This means key conventional prior art laser ablation components would fail within 1 hour or less, and sometimes within 15 minutes. This is true of prior art small motors, optical coatings, electronic circuits—especially integrated circuits, laser heads, power supplies, sensors, and video cameras. Additional prior art components subject to failure on a somewhat longer time scale (still problematic) include cables, connectors, insulation on wires, o-rings, lubricants, adhesives, and a variety of plastic or polymer parts, as well as conventional optics. Laser mirrors (thin film dichroic) are particularly susceptible to radiation damage. Conventional prior art analytical UV laser ablation systems can't even withstand 1 day in the hot cell with high activity nuclear waste samples which nevertheless require analysis.

In a March 2007 government report (07-DESIGN-042, U.S. DOE Office of River Protection, contract DE-ACO5-76RL01830), the US DOE has designated laser ablation as a critical technology element (CTE) necessary for the $12.3B nuclear waste processing (vitrification) plant now under construction at the DOE Hanford, WA site. It would therefore be desirable if an invention comprehensively rad-hardened laser ablation system could be developed to withstand 1,000-2,000 rads per hour for an expected useful life of 7-12 years in that environment, instead of failing within less than a day, or less than 1 hour. A total radiation tolerance of 100 million rads total accumulated exposure is therefore desired for an invention comprehensively rad-hardened laser ablation system for nuclear waste analysis. With prior art UV laser ablation systems failing within 500-1,000 rads total accumulated exposure, it is clear that there remains a need for a new invention to meet DOE radiation hot cell needs.

SUMMARY OF THE INVENTION

The invention laser ablation system of FIGS. 2A, 2B replaces a conventional prior art dichroic mirror beam combiner (((6)—FIG. 1) coaxially combining the final segment of the laser optical path with the initial segment of a white light viewing system) with an invention angled mirror-with-hole (25, 26)—FIGS. 2A, 2B, 9A, 9B. This allows an invention focused UV laser beam (7, 10) to pass (unaltered) through the hole (26) forming a focused spot on the solid material surface (11, 24) below, while the invention observer "white light view" (18-20, 22) of said solid material surface is obtained with the invention angled mirror perimeter (33) concentrically surrounding the hole (26) and said UV laser beam (7, 10) passing through said hole (26), and said white light view obtained in an area encompassing and concentrically surrounding said focused laser spot. The advantage of this invention is optical "decoupling" of the UV laser beam (7, 10) from the "white light" observer view (18, 20, 22, 28), even though the two invention light paths coaxially share a superimposed path segment (10, 18).

Invention optical decoupling of the two paths is desirable for UV laser ablation to allow separate optical optimization of the invention laser path and the invention white light camera view. (A prior art "coupled path" does not permit this). The invention UV laser objective lens (8) focuses only the UV laser light, and does not affect the invention white light camera view which may then be separately focused with an invention high quality achromatic visible lens (21), optimized separately for the invention camera (22), and thereby eliminating chromatic aberration from the camera view (22, 28). This invention allows the best laser ablation characteristics to occur (24) simultaneously with the best quality observer (camera) image (22).

The "mirror-with-hole" invention laser ablation viewing system depends on a second aspect of the generalized laser ablation invention which is the use of substantially longer-than-normal focal lengths (greater than F=40 mm, and preferably greater than F=100 mm) in the invention laser objective focusing lens (8) and substantially longer-than-normal invention laser object distances (4→8). The substantially longer-than-normal invention focal lengths "F", and substantially longer-than-normal invention laser object distances "O" of the invention give rise to a substantially longer-than-normal invention laser spot image distance "I" (8→24) according to the laser objective lens formula:

$$1/F = 1/O + 1/I$$

where F is the focal length, O is the object distance (4→8) and I is the image distance (8→24), and this increased invention laser spot image distance (I) allows enough room between the invention objective lens (8) and the solid sample surface (11, 24) and sample cell (9, 23) to fit (in) the invention "mirror-with-hole" (25, 26), which could otherwise not be fitted in (not enough room) below the FIG. 1 conventional prior art analytical laser ablation objective lens (8) which is limited by the prior art short focal length geo-bias.

A third preferred invention aspect, namely that of large focused spot analysis in SRM analytical laser ablation is also facilitated by the larger-than-normal focal length invention laser objective lens (8) which allows a reduction in demagnification ratio, yielding larger invention SMR homogeneous laser spot diameters—e.g. >0.2 mm and up to 1.5 mm or more, and this, in turn, permits the use of much larger invention pulsed UV excimer or SRM (frequency multiplied) Nd-YAG lasers (1) greater than 12 mJ (@ 266 nm) and, in a non-limiting example, up to 300 mJ at 266 nm without exceeding the IIR of solid samples. Up to 25× higher invention ablation rates are thereby enabled, compared to conventional (geo-biased) prior art UV analytical laser ablation, without exceeding the sample HR. Substantially enhanced invention analytical laser ablation sensitivity in the ppb range may thereby be achieved, compared to reduced (ppm range) sensitivity of prior art analytical laser ablation. Embodiments with excimer and 213 nm or 193 nm (frequency multiplied) Nd-YAG lasers may also be envisioned and these are within the scope of the invention, as well as diode pumped lasers, longer wavelength lasers and femto-second lasers. Additional invention embodiments using a long focal length mirror objective focusing element may also be envisioned and are within the scope of this invention.

The longer focal length invention laser ablation objective lens (8) exhibits advantage in providing an opportunity for greater invention laser ablation bulk analysis sensitivity of a solid surface, since an invention longer focal length lens (e.g. F>40 mm, and especially F=150 to 400 mm in a nonlimiting example) is naturally accompanied by less demagnification in the final SMR focused laser spot size (24), yielding significantly larger invention SMR laser spot diameters (>0.2 mm, and preferably 0.4-1.6 mm in a nonlimiting example), and therefore allowing use of more powerful invention excimer and SMR lasers (1) without exceeding the IIR and overpowering (e.g. shattering, cracking, large particle expulsion, etc.) the sample. Essentially, the same energy density (joules/cm$^2$) within the sample IIR may be used from a larger invention laser, but also focused into a larger invention spot diameter (24) to ablate more material, under (desirable) IIR conditions. The result is a larger solid sample area is ablated at the same (optimized) energy density by the invention.

The final result is that substantially more sample vapor, smoke, and/or particulate aerosol is produced within the sample IIR during ablation with the preferred embodiment large homogeneous spot, high powered, excimer or SMR based Nd-YAG laser ablation invention. Invention ablation rates are therefore desirably stable and consistently higher for the same sample material and energy density. This gives rise to higher invention signals in the external analytical instruments (15) to which the vapor, smoke, and/or particulate aerosol from the invention are directed for analysis. The higher signal produced from large area IIR invention ablation gives rise to enhanced invention analysis sensitivity, and the combined invention and external analytical instrument (15) are capable of 10-25 fold more analytical sensitivity, depending on how much bigger the invention laser (1) and correspondingly selected invention laser spot diameter (facilitating ablation within the sample IIR) are chosen to be.

Essentially, the invention employs substantially longer focal length laser objective lenses (8) yielding an option for larger spot diameters in invention excimer and SMR analytical UV laser ablation. Instead of limiting to 0.2 mm maximum spot diameter, which is the largest focused spot normally available in conventional prior art excimer and SMR analytical laser ablation, the invention will allow spot diameters of up to 1.5 mm or more in a nonlimiting example, if a sufficiently large excimer or SMR invention laser (1) is substituted to "make up" the former prior art energy density in the invention larger spot diameters. This will easily allow invention laser ablation analysis in the ppb (parts per billion) or sub-ppb range instead of conventional (part per million) sensitivity limits of prior art analytical laser ablation.

Referring to FIG. 2A, a preferred embodiment invention excimer or SMR Nd-YAG laser (1) is substantially more powerful than corresponding lasers used in prior art analytical laser ablation. This aspect of the FIG. 2A invention analytical laser ablation invention is enabled by the unusually long focal length of invention laser objective lens (8) which has focal length greater than F=40 mm (and preferably F=150 mm or more in a nonlimiting example) and is about 4× longer focal length (in a nonlimiting example) than prior art excimer or SMR Nd-YAG analytical laser ablation, and which enables nominally 4× less demagnification and nominally 4× larger focused invention laser spot diameter (24) according to the parametric equations (using earlier defined terms):

$$1/F=1/O+1/I \text{ and } m^{-1}=O/I$$

With nominally 4× larger (nonlimiting example) invention excimer or SMR Nd-YAG focused spot diameter (24), the FIG. 2A preferred invention embodiment can employ a 16× larger SMR invention laser (1) without exceeding the ideal irradiance range (IIR in J/cm$^2$/ns) of solid samples. The prior art laser ablation system of FIG. 1A cannot do this, owing to a 4× (or more) shorter focal length prior art objective lens (8) which does not facilitate focused laser spot diameters above 0.2 mm in prior art analytical laser ablation systems using excimer or SMR Nd-YAG lasers.

Further manipulation of invention object and image distances according to the above listed parametric equations would actually allow up to a 1.5 mm invention spot diameter and a 30× larger invention laser without exceeding the IIR of solid samples. The combination of an invention 4-30× larger laser with oversized invention spot diameters in the range of 0.4-1.5 mm will yield substantially higher ablation rates at typical sample IIR's and more bulk analysis sensitivity (e.g. 4-30× more) than prior art excimer or SMR Nd-YAG analytical laser ablation systems. Ultra-trace bulk solids analysis in the parts-per-billion (ppb) range may thereby be achieved by a preferred invention embodiment.

By wide range operational repositioning of at least two laser "steering" mirrors (e.g. mirrors 30, 31 in FIG. 2A being moved to alternate positions in FIGS. 3A-B, 4A, and 5) in a preferred invention folded detour laser path coupled with wide range operational repositioning of a laser objective lens (8), a preferred embodiment of the invention further provides for wide range, operationally variable demagnification ratio in the focused invention laser spot size (24). The at least two preferred invention laser steering mirrors (30, 31) may be manually relocated to alter the length of a preferred invention folded detour laser object path (FIGS. 2A, 4A, and 5 or FIGS. 3A-3B), or they may be mounted on a preferred embodiment invention precision motorized track (41) with a lead-screw drive (42) as in FIG. 6 for motorized alteration of the preferred invention embodiment folded laser object path length. The invention laser objective lens (to be repositioned) may be manually repositioned or in a preferred FIG. 2B embodiment, it may be mounted on a gantry (35) coupled to a motorized track (36) with a lead-screw for motorized alteration of the overall invention focused laser spot demagnification ratio in combination with a FIG. 6 motorized repositioning or a FIGS. 3A-C manual repositioning of the invention mirrors 30, 31.

It has been noted that movement of laser steering mirrors 30, 31 in a direction parallel to the beam path from 29-30 in FIGS. 3A-C and in FIGS. 2A, 4A, and 5. In a second embodiment which may function alone, or in combination with parallel movement of mirrors 30, 31, FIGS. 4B-J illustrate that at least one folded optical detour path may be created which is perpendicular to the original FIG. 2A laser path segment between 31 and 6. By inserting various mirrors 126-128 with a perpendicular motion of wedge mount 125, various folded optical detour paths including 128→129→134→135 (FIG. 4C), 127→130→133→136 (FIG. 4D), and 126→131→132→137 (FIG. 4E) are enabled which lengthen the path segment between 31 and 6 by varied optical detour amounts, while still directing it coincidentally (coaxially) with path 7 through the objective focusing optic 8 focusing (with demagnification) to solid target sample 11. In a third embodiment, FIGS. 4G-J illustrate that a pair of single larger mirrors 138, 139 can replace the illustrated six individual mirrors 126-128 and 135-137 on the movable wedge mount 125 and accomplish essentially the same set of optical detour path elongations.

Speaking broadly, relocation of the movable wedge mount 125 or relocation of the at least two invention laser steering mirrors (30, 31) varies the invention object distance, O. Relocation of either the sample (11) or the invention objective lens (8) varies the invention image distance I according to the lens formula given earlier. The resulting changes in O and I then give rise to an alteration of the invention demagnification ratio m$^{-1}$, such that:

$$m^{-1}=O/I$$

The greatest sensitivity for laser ablation analysis for a given material and a given laser size will occur with the laser operating at 100% output power and the full laser beam focused into a spot diameter yielding the ideal irradiance range (IIR) for that sample material and laser wavelength. Since sample materials vary widely in values of IIR, it would be desirable to have a wide range of full power irradiance values available for a single analytical laser ablation system. This is not possible with prior art laser ablation systems which have a fixed object distance (O). The lens formula dictates that for a fixed prior art object distance (O) and a fixed prior art focal length (F), the prior art image distance (I) and therefore the prior art demagnification ratio (m$^{-1}$=O/I) will also be fixed. With a fixed prior art demagnification value, the irradiance at 100% laser power output will not vary, and so variations in IIR for different samples may not be matched at full power with a prior art system having fixed O and fixed F (yielding fixed I and fixed m$^{-1}$). Some samples may fall into the fixed IIR of a given prior art system at full power, but many others will fall outside of their IIR, thus limiting the sensitivity of prior art analysis, and the reliability of prior art calibration.

Preferred invention embodiments shown in FIGS. 2A-6 solve this problem by allowing substantial practical variation of object distance (O) by as much as a full meter or more of path length. Such a large practical variation of invention object distance (O) produces a correspondingly large variation in invention image distance (I) and invention demagnification ratio (m$^{-1}$), thus enabling the FIGS. 2A-6 preferred invention embodiments to serve as the first known wide range, variable demagnification ratio analytical laser ablation system, capable of ablating any solid material within its IIR, and at 100% laser power output, thus achieving maximum sensitivity and calibration reliability for bulk analysis of all materials which is possible for a given laser. To achieve the required large variation in invention object distance, the dichroic mirror pair (30, 31) may be moved right or left in the FIGS. 2A, 4A, 5 and 6 diagrams, thus shortening or lengthening the object distance in the invention folded detour path or movable wedge mount 125 may be moved up or down in the FIGS. 4B-J diagrams, or a combination of mirror 30, 31 movement and wedge 125 movement may be employed. A corresponding vertical relocation of sample 11 or invention objective lens (8) (or a combination of the two) is needed to satisfy the lens formula (1/F=1/O+1/I) and keep the laser spot image (24) focused at sample surface (11). Invention mirrors 30, 31 and/or wedge 125 and sample 11 and/or objective lens 8 are thus positioned to maintain a focused laser spot image (of aperture 4) on the sample surface (11, 24). In one preferred invention embodiment, the mirrors 30, 31 and/or wedge 125 and objective lens (8) are moved in such a way that the lens formula (1/F=1/O+1/I) is always kept satisfied as the focal plane (24) remains fixed. The demagnification ratio (m'=OA) and the irradiance are however greatly altered with these invention mirror and lens movements, and a wide variety of sample IIR may thereby be ideally matched by the invention.

If desired, the repositioning of invention mirrors (30, 31) and/or wedge 125 and invention objective lens (8) may be done manually through use of invention kinematic mounts to allow a variety of pre-set invention demagnification ratios. If the invention components are kinematically mounted (39) then a separate set of pre-aligned kinematically mounted invention mirrors (e.g. 30, 31, 39 in FIGS. 3-5) may be provided for each different invention path length configuration of an invention multi-position (multi-configuration) folded laser path and may be quickly interchanged to effect rapid and convenient operational change of the invention demagnification ratio, without a system realignment.

It should be noted that vertical motion of lens 8 on a precision motion stage or gantry (see 35, 36 in FIG. 2B) may or may not require invention laser system realignment, however motion of the mirror pair 30, 31 will most certainly require invention laser system realignment to keep the focused laser spot exactly centered on sample position 24, taken as a reference position.

To achieve operational invention laser system realignment upon substantial relocation of mirrors 30, 31 and/or lens 8, mirrors 30, 31 may be mounted on a plate (39) and plate (39) may be kinematically mounted to the invention optical platform (40). Pre-alignment of invention mirrors 30, 31 for a given plate (39) position on the invention optical platform (40) will then assure that overall invention alignment is maintained whenever plate (39) is in it's pre-aligned optical platform position. A key feature of this preferred invention embodiment is that plate (39) is only used in one position, so each time it is installed in position, its kinematic mount ensures that the pre-aligned mirror (30, 31) condition is maintained. To change plate positions (relocation), a different invention plate with a separate invention mirror pair must then be substituted, with the new mirror pair being pre-aligned for the new plate position (also kinematically mounted to the new position). Essentially, this embodiment of the invention uses a new pre-aligned mirror pair and kinematically mounted plate for each available mirror position. To operationally relocate the mirrors, a new mirror pair (and plate) is selected for each position, and each separate mirror pair is pre-aligned to its own location on the optical platform (40). The required number of mirror pairs must equal the required number of different mirror positions. Operational relocation is achieved simply by demounting the previous mirror pair (and plate) from its quick-release kinematic mount, selecting a new mirror pair (pre-aligned for the new position), and quickly clamping it into its designated (new) position. The pre-alignment characteristic of the newly selected mirror pair makes it unnecessary to re-align the system upon installation of the new pair.

Alternatively, a preferred motorized FIG. 6 embodiment of invention mirror and objective lens reconfiguration (repositioning) to effect invention variable demagnification ratio may be computer controlled if the motors are precision digital stepping motors. In this case a single pair of the at least two invention laser steering mirrors (30, 31) would be moved to effect object distance variation in the invention folded laser path.

Path length variation by the folded path detours of FIGS. 4B-J have the special benefit of having fixed, pre-aligned mirror settings on a precision gimbaling mount for each mirror in the series 129-134 which automatically maintain alignment of image 24 at a preselected reference location on sample 11 as wedge 125 is relocated to its various positions which are preferred to be kinematically stabilized at each location. Kinematic stabilization ensures that wedge 125 is consistent in its locations, such that the pre-aligned, preset mirrors 129-134 always ensure that image 24 remains centered at the preselected reference location on sample 11 as wedge 125 is relocated.

This level of invention system adjustability allows users of an invention analytical laser ablation system to operationally adjust the maximum focused laser spot size to keep invention focused laser energy and irradiance within the IIR of each and every sample type without need of realignment, regardless of how narrow an individual IIR range may be and how widely the IIR may vary from one material to the next. When coupled with the use of larger invention lasers, this invention operationally adjustable maximum spot size feature provides for the maximum possible ablation rate, sensitivity and calibration accuracy (and reliability) possible for each sample type, without shattering the sample or exceeding its IIR, even in the face of different materials with widely varying IIR. Such a characteristic has never before been available in a prior art laser ablation system, and it allows the full invention laser power to be 100% utilized in an optimized way on an operation basis for each sample analysis, and provides for part-per-billion (ppb) analysis of solid samples by invention UV analytical laser ablation, instead of the conventional ppm sensitivity limits of prior art systems.

A further characteristic of a preferred embodiment invention laser ablation system operationally variable demagnification ratio feature is automatic realignment of the invention laser beam following a change of invention demagnification ratio. Normally, if folding mirrors were repositioned to vary the laser path length, a realignment of the laser mirror system would be required. This would normally have to be painstakingly performed using precision angular adjustment controls for the mirrors and also using alignment targets and bore sight tooling. Mirror alignments made in one folded path configuration will not hold when the folded path is reconfigured (to change its length) by relocating one or more mirrors.

For a manually reconfigured (FIGS. 2A, 3A-C, 4A, and 5) embodiment of the invention variable demagnification feature, the aforementioned pre-aligned mirrors (30, 31) on kinematic mounts (39, FIGS. 3A-C) will suffice to maintain invention laser beam alignment following a change of path length, if a different (separate) invention pre-aligned mirror pair (30, 31) is devoted to each pre-set location in the invention variable folded detour path. In one non-limiting example, if there are to be 8 different invention preset demagnification ratios involving 8 different mirror pair locations, then 8 different pre-aligned mirror pairs (30, 31) would be needed, one (pre-aligned) pair (30, 31) for each demagnification ratio to be operationally selected. This requires extra mirrors—more than a prior art fixed demagnification system, but the invention mirror pairs are each pre-aligned, operationally demountable, and kinematically stabilized for precise, quick interchange, so the operational change of invention demagnification ratio is relatively easy to perform, and requires no system realignment after changing the demagnification.

An even more convenient (more highly preferred yet) embodiment of the invention may be envisioned without extra mirrors, if a further modification to the preferred FIG. 6 motorized invention embodiment is considered. In the preferred FIG. 6 motorized embodiment, the invention laser ablation system rapidly achieves automatic laser beam realignment through the folded detour path mirror system, when the at least two invention mirrors (30, 31) are relocated to alter the invention folded path length, by virtue of invention small precision digitally controlled stepping motors (43) mounted on the precision gimbaling mirror mounts controlling the invention mirror angles. Preset stepper motor addresses may be pre-determined (through a pre-alignment exercise) for each different invention folded detour path length for the laser. Each time the invention folded path length and demagnification ratio are changed by repositioning the at least two invention mirrors (30, 31), stored values of (pre-aligned) invention stepper motor (43) address may be retrieved by the invention computer that correspond exactly to the new alignment angles of the at least two invention mirrors (30, 31) for the new position, and the invention mirror angles may thus be quickly reset to their new pre-determined alignment for each invention demagnification ratio.

A preferred embodiment of the invention involves actual relocation of the same mirror pair 30, 31 to one or more preset locations along a precision linear track. Precision micrometer settings on the gimbaling mirror angle adjustments of one or both of the two mirrors may be pre-determined to maintain overall system alignment for each preset location on the linear track. Pre-determination of mirror gimbal micrometer settings would be done in a preliminary setup alignment exercise performed for each preset location on the track. Once a full set of micrometer settings has been determined (separate settings for each preset track location), then those micrometer settings simply have to be replicated (for that track position) each time the mirror pair is moved to a new location. This may be done manually with precision micrometer settings, or digital stepping motors may be attached to the gimbaling adjustments and then the pre-determined stepper motor addresses set for the gimbaling adjustments on the mirrors corresponding to a given track location selected. Separate stepper motor addresses (mirror gimbaling adjustments) would be predetermined for each preset track location. A computer may store these stepper motor addresses and then recall them (and reload them to the stepper motors) each time the mirror pair is moved between preset locations.

Invention mirror pair motion to any location between two preset locations on the linear track may be dealt with by computer interpolation between the gimbaling stepper motor addresses for the bracketing preset locations. In this way a full range of continuously variable demagnification ratios may be operationally obtained with automatic system realignment. An invention operator need only enter the desired magnification ratio into the system computer and a digital stepping motor will automatically relocate the mirror pair along the linear track and additional stepping motors will automatically realign the mirrors to a preset or interpolated alignment corresponding to the selected track position.

In addition, the invention laser objective lens may be positioned on a focus track and controlled by the computer to keep the lens formula (1/F=1/O+1/I) satisfied (image focused) for a fixed sample position, as the mirrors move. Essentially, when a new demagnification ratio is specified by the invention user, the computer will solve the parametric equations (1/F=1/O+1/I and $m^{-1}$=O/I) for a fixed value of F and the specified $m^{-1}$ to yield corresponding values of O and I which determine the mirror and lens placements for that $m^{-1}$. Then the computer will look up (or interpolate) new pre-determined pre-alignment values of mirror gimbaling (angle) adjustments to restore system alignment. This invention feature is completely new to analytical laser ablation and it will facilitate operational selection of a wide variety of demagnification ratios to meet the application-specific IIR requirements of virtually any solid sample, while allowing the full available laser power to be used for each analysis. This will maximize invention sensitivity and also maximize overall analytical instrument calibration precision, accuracy, consistency, and reliability.

A further preferred embodiment to extend the range of usable spot diameters and demagnification ratios would include variable focal length in the invention objective lens. To facilitate this, interchangeable invention objective lenses of varying focal length may be employed, including (in one preferred embodiment) a rotary turret containing at least two invention objective lenses of different focal length. Invention zoom laser objective lenses and variable focus laser objective lenses may also be envisioned in other embodiments, either alone, or in combination with other lenses (individually interchangeable or on a turret) so long as they have the requisite UV transmission properties.

In one preferred embodiment, the invention objective lens (or turret) may be mounted on a precision motion stage for repositioning (as invention laser mirrors are relocated). In another FIG. 6 embodiment (see especially FIG. 2B, items 8, 25, 26, 21, 27, 22), the invention objective lens, mirror-with-hole, and visible "white light" achromatic lens and camera may all be mounted on a gantry (35, 66), such that the entire gantry moves to reposition these optics, as invention laser mirrors are relocated.

In one preferred embodiment, the invention gantry may also be precisely moved (up and down) to focus the laser spot image and camera object planes (if coincident) onto the solid sample surface. In another embodiment the invention camera (22) may be relocated to shift the white light object plane to keep coincident with the laser spot image plane which may move upon invention laser mirror and laser objective lens repositioning to achieve varied invention demagnification ratios.

In another preferred embodiment, the solid sample (and/or sample cell) may be moved on a precision vertical motion stage to achieve focus of the laser spot image and camera object planes to the sample surface.

Invention modularity may accommodate lasers of widely differing size and power on a single "flex" platform, without repositioning or reconfiguring the remaining optics.

A final advantage of the "mirror-with-hole" invention laser ablation viewing system is that a prior art thin-film coated dichroic mirror ((6) in FIG. 1) is replaced by the invention mirror-with-hole (25, 26 in FIGS. 2A-B, 9A-B) at an invention optical convergence point of the two (laser and camera) paths, and eliminating the (radiation damage prone) thin-film coating of a prior art dichroic mirror, allows a preferred embodiment invention UV laser ablation mirror-with-hole to function undamaged for at least 100,000 rads total accumulated radiation exposure (in a nonlimiting example, and e.g. for 100 million rads in a preferred embodiment) in a radiation "hot cell" for analysis of high activity nuclear waste, if the invention laser beam (5, 7) originates outside of the "hot cell". (See FIGS. 7A-B, in which the entire FIGS. 7A-B invention upper module apparatus is located on top of the hot cell and the emergent FIGS. 7A-B laser beam (7) proceeds downward into the hot cell through a small opening in the hot cell ceiling), and the invention final line-of-sight mirror (6)—line of sight to a radioactive solid sample in ablation cell (23) of the invention lower module (See FIG. 8A) and also the invention camera (22, See FIGS. 8A-B) are rad-hardened and/or shielded, respectively. To rad-harden invention line-of-sight mirror 6 (FIGS. 7A-B), it cannot be a prior art thin film dichroic laser mirror (subject to rapid radiation damage), and a fully aluminized invention line-of-sight mirror would have to be substituted instead. (Conventional prior art thin film dichroic mirror coatings are rapidly destroyed by radiation damage at 1,000 rads/hour exposure in an activated radiation "hot cell".) The invention aluminized final line-of-sight laser steering mirror has a reduced reflectance of about 96% R when new, compared with a new (non-irradiated) prior art dichroic mirror (99.7% R), but after a short time (e.g. within a few minutes or hours) of exposure to high activity nuclear waste (e.g. 1000 rads/hr), the prior art dichroic mirror will be destroyed and the invention aluminized final line-of-sight steering mirror will still be 96% R. A small percentage reduction (e.g. 3-4%) of initial reflectance in the invention line-of-sight steering mirror thus extends the invention useful lifetime to about 6-12 years, rather than 6-12 minutes (or hours) lifetime for a prior art system. A preferred FIG. 7A-B, 8A-B, 9A-D rad-hardened embodiment of the invention analytical UV laser ablation system is thereby enabled for the analysis of solid nuclear waste, or a witness coupon of the nuclear waste which has been vitrified into radioactive glass, with a small witness coupon to the vitrification process being presented for analysis in ablation cell 23 (11, 24).

One preferred invention embodiment therefore employs a split architecture invention laser ablation system for a radiation hot cell as in FIGS. 7A-B, 8A-B, in which an invention laser (1, FIGS. 7A-B) and invention laser steering mirrors (29, 30, 31, 6) are located outside of the hot cell with a beam (7) from the invention laser entering the hot cell through a window in the hot cell, and in which the invention FIGS. 8A-B and 9A-D "lower module" comprising an invention long focal length (uncoated) laser objective lens (8), mirror-with-hole (25, 26), invention uncoated view camera lens (module 66 in FIG. 8A, similar to module 66 of FIG. 2B except achromatic lenses (21) are uncoated), invention shielded view camera (67, 22), invention ablation cell (23), invention automated sample changer (44-46, 81-84), invention ablation cell translational motion stages ((44-46, 89, 47-49, 50-52) facilitating sample focus, line scan ablation, and raster pattern ablation), and invention energy meter (90) is located inside the hot cell, In a preferred FIGS. 8A-B embodiment, all hot cell components (key components and subsystems) are modularized for quick dismount and replacement by a hot cell manipulator arm and gripper claw. Kinematic mounting of invention hot cell laser ablation components and subsystems is an invention feature which facilitates replacement by manipulator with optically pre-aligned replacement components and subsystems, thereby eliminating the need for "manned entry" (along with eliminating the need for difficult and expensive hot cell decontamination associated with "manned entry") for the service replacement exercise.

In one preferred embodiment, said invention FIGS. 8A-B "lower module" components in the hot cell are rad-hardened and/or radiation shielded and/or exhibit placement "at distance" from radioactive samples, to permit each said invention lower module component and the overall invention lower module to withstand at least 100,000 rads and preferably up to 100 million rads total lifetime radiation exposure prior to a radiation damage failure point, and in which additional invention laser ablation components receiving "line of sight" radiation outside the hot cell, such as a final invention laser beam steering mirror (6) directing the external invention laser beam (7) into the hot cell is rad-hardened to withstand radiation exposure, and in which an invention valve module, directing the flow of carrier gas and/or purge gas to the invention ablation cell, is a rad-hardened valve module capable of withstanding radiation exposure, In the various radiation hot cell embodiments so far listed, rad hardening is accomplished by the components being manufactured materials selected from a list prepared and published by nuclear testing groups such as CERN, said list being comprised of materials tested and found not to deteriorate under accumulated radiation exposure to at least 100,000 rads and preferably up to 100 million rads in CERN agency reports and testing programs.

This includes construction materials, wiring insulation, connectors, cables, motors, lubricants, seals, and optics. The invention uses CERN approved rad-hardened materials throughout all of its components installed in the hot cell installation. No prior art laser ablation system has done this. Cements and glues are not tolerated. Certain polymers (e.g. Teflon) are not recommended. Electronics (especially integrated circuit chips) must be outside the hot cell (or heavily shielded), with only control voltage and current lines entering. Laser ablation video cameras and energy meters must be rad-hardened and/or heavily shielded from line-of-sight radiation in the hot cell. All of these properties are claimed for the invention laser ablation system, as no prior art laser ablation system employs them, and the invention laser ablation system does employ them and an invention prototype has been built and successfully installed in a radiation hot cell at DOE Hanford site, with radiation damage immunity designed to withstand 100 million rads total lifetime accumulated exposure. At 1000-2000 rads/h, and normal work shifts, the invention prototype is expected to last 6-12 years before failure due to radiation damage. (Prior art laser ablation systems would last maybe 6-12 minutes, or maybe an hour at most in this environment). Higher or lower levels of rad-hardening may be incorporated and still be included in the scope of this invention.

A final advantage of the "mirror-with-hole" invention laser ablation viewing system is that a conventional prior art thin-film coated dichroic mirror ((6) in FIG. 1) is replaced by the invention mirror-with-hole (25, 26 in FIG. 9A-B) at an invention optical convergence point of the two paths, and eliminating the thin-film coating of a prior art dichroic mirror allows a preferred embodiment invention UV laser ablation to function in a radiation "hot cell" for analysis of high activity nuclear waste, if the invention laser beam (7) originates outside of the "hot cell" (see FIGS. 7A-B), and the invention final line-of-sight mirror (6)—line of sight to a radioactive solid sample (11, 24) and also the invention camera (22) are rad-hardened and/or shielded (67), respectively. To rad-harden invention line-of-sight mirror (6), it cannot be a conventional prior art dichroic laser mirror (subject to rapid radiation damage), and a fully aluminized invention line-of-sight mirror is substituted by the invention instead. (Conventional prior art thin film dichroic mirror coatings are rapidly destroyed by radiation damage at 1,000 rads/hour exposure in an activated radiation "hot cell".) The invention aluminized final line-of-sight laser steering mirror has a reduced reflectance of about 96% R when new, compared with a new (non-irradiated) prior art dichroic mirror (99.7% R), but after a short time (e.g. within a few minutes or hours) of exposure to high activity nuclear waste (e.g. 1000 rads/hr), the prior art dichroic mirror will be destroyed and the invention aluminized final line-of-sight steering mirror will still be 96% R. A small percentage reduction of initial reflectance in the invention line-of-sight steering mirror thus extends the invention useful lifetime to about 6-12 years, rather than 6-12 minutes (or hours) lifetime for a prior art system. A preferred FIG. 7A-B, 8A-B rad-hardened embodiment of the invention analytical UV laser ablation system is thereby enabled for the analysis of solid nuclear waste (11, 24).

One preferred invention embodiment employs a split architecture invention laser ablation system for a radiation hot cell as in FIGS. 7A-B, 8A-B in which an invention laser and invention laser steering mirrors are located outside of the hot cell with a beam from the invention laser entering the hot cell through a window in the hot cell, and in which the invention "lower module" comprising an invention long focal length (uncoated) laser objective lens, mirror-with-hole, invention uncoated view camera lens, invention shielded view camera, invention ablation cell, invention automated sample changer, invention ablation cell translational motion stages (facilitating sample focus, line scan ablation, and raster pattern ablation), and invention energy meter are located inside the hot cell, and in which said invention "lower module" components in the hot cell are rad-hardened and/or radiation shielded and/or exhibit placement "at greater than normal distance" from radioactive samples, to permit each said invention lower module component and the overall invention lower module to withstand at least 100,000 rads and preferably up to 100 million rads total lifetime radiation exposure prior to a radiation damage failure point, and in which additional invention laser ablation components receiving "line of sight" radiation outside the hot cell, such as a final invention laser beam steering mirror directing the external invention laser beam into the hot cell is rad-hardened to withstand radiation exposure, and in which an invention valve module, directing the flow of carrier gas and/or purge gas to and from the invention ablation cell, is a rad-hardened valve module capable of withstanding radiation exposure. The invention prototype laser ablation system installed in the hot cell at DOE Hanford site exhibits all of the above embodiment characteristics and is fully functional.

In preferred FIGS. 9B, 8A-B embodiments of the invention (either "cold" or rad-hardened) laser ablation system, a demountable sample ablation cell for laser ablation analysis is employed in which the ablation cell components assemble and seal by vertically stacking (mating) components, without using fasteners, tie downs, latches, clamps, snaps, bolts or any other fastener or clamping means. Assembly and low pressure sealing is simply by stacking the mated components vertically, and demounting is simply by unstacking the components (with simple "lift off" means), without need to remove or release any fastener, latch, or clamp. In a preferred embodiment invention demountable sample ablation cell, gas seals are achieved by a weight compression factor, with upper cell components having sufficient weight to deliver a gas sealing force to mating lower cell components. The seals or a combination of seals are selected from among a group comprising tapered seals, gaskets, and o-rings and in which the selected seals are compressed to their sealing points solely by the weight of stacked overhead cell components.

If the weight of stacked overhead cell components becomes excessive, a preferred FIG. 8A-B embodiment of the invention employs a demountable sample ablation cell (23, 76, 80) in which a counterbalancing force (95-102) is applied in compound linkages and levers to offset the combined weight of stacked ablation cell components (23) and FIG. 9B (all) without diminishing sealing forces below their gas sealing points, in order to allow "light duty" X, Y, Z translational stages to control the combined stacked cell positioning. The counterbalancing force may involve a spring loaded plate or platform, or it may involve at least one counterbalancing weight.

In a preferred invention embodiment, an invention sample changer for laser ablation analysis may cause samples or sample holders (containing samples) to be sequentially placed in proximity to an ablation cell to effect sequential laser ablation events and sample analysis by an external ICP, ICP-MS, or FAG-MS instrument, in which a sample changing means places at least a first sample in proximity to an ablation cell, and in which said sample changing means removes said first sample after laser ablation analysis, and in which said sample changing means then places at least a second sample in proximity to said ablation cell.

In a preferred embodiment sample changer, samples may be sequentially lifted out of a counter bore in a movable platform (83, see FIG. 9A) selected from a movable platform group comprising a rotary carousel, an R-Theta rotating/sliding tray, an X, Y sliding tray, or a linear feed-through tray or conveyor, said samples or sample holders (containing samples) being lifted out of said movable platform by a mechanized push rod (81, 106) which pushes upward through a through-hole ((124)—FIG. 9C, (24)—FIG. 8A) contained within the counterbore, and lifts the samples (11) or sample holders (82, containing samples 11) up and out of the movable platform 83, and in which the lifting action further places the samples or sample holders in proximity to a laser ablation sample cell as in FIG. 9C.

In a preferred embodiment a segment (81) of the push rod o.d. diameter is less than the i.d. of the through hole (124) in the movable platform, to an extent which allows horizontal motion of the push rod to effect a line scan, or x, y raster scan, or R-Theta raster scan of the sample horizontally in the laser beam. The invention sample changer's movable platform sequentially presents the samples or sample holders (containing samples) of a group "one at a time" for the push rod to sequentially lift into proximity to the laser ablation sample cell, so that each sample may be analyzed sequentially (in turn) by laser ablation analysis. Referring to FIGS. 9A-C, the sample changer lifting action seals the sample or sample holder (82) (containing a sample (11)) against or into a sample ablation cell (23) via weight-stacked matching tapers (an o.d. taper (82) on the sample holder mating to an identical i.d. taper (108) in the base of the sample cell).

The sample changer may continue push rod (81) lifting action after sealing to further lift the sample cell and sample or sample holder (containing a sample) as a stack, said lift proceeding upward to lift the stack out of a stationary sample ablation cell holding platform (75) and further continues the lift until the upper surface of the sample reaches a laser ablation focal plane (24) or a specified defocused laser ablation plane. The mechanized push rod and lift stage is further mounted atop an X, Y (47-49, 50-52) or R-Theta translational stage capable of offsetting the push rod with stacked sample holder, sample, and sample ablation cell in a linear horizontal motion (see FIG. 9D offset (24, 11, 75-76, 47-48) or an X, Y horizontal raster pattern, or an arc motion or an R-Theta raster pattern for laser ablation or to selected stationary horizontal offset positions for laser ablation after lifting and focusing.

In another FIG. 10 preferred embodiment, the invention sample changer may keep the support rod (81) vertically stationary and employ the movable platform (83) to position a sample over the support rod and then lower the sample or sample holder (containing sample) onto the support rod and the platform continues to lower after the sample holder engages the top of the support rod, such that the platform lowers itself to clear the bottom edge of the sample or sample holder. In this embodiment it is preferred that invention laser focusing is be performed by vertical rise or fall of an invention overhead gantry (66) containing at least the laser objective lens (8). In a preferred embodiment, the invention gantry would also support the invention visible white light viewing system and mirror-with-hole (25, 26—see FIG. 2B). In a preferred FIG. 10 embodiment, the gantry also functions to raise or lower the sample ablation cell enclosure (23) over the stationary sample or sample holder (containing sample).

In another embodiment, an invention sample cell for laser ablation has the sample cell closed on the top and open on the bottom, and in which the open bottom is positioned in proximity to a sample surface, and in which carrier gas enters the cell via the annular space between the bottom of the sample cell and the top of the sample surface, and in which an outer concentric "skirt" affixed to the sample cell o.d. provides a compliant seal to the sample, and in which carrier gas is entered into the annular space from the skirt. In this embodiment, the sample cell is horizontally stationary, but the compliant seal is a sliding seal which allows the sample to move horizontally without breaking the seal. In one embodiment, the i.d. of the bottom of the invention sample cell and skirt are both smaller than the perimeter of the sample, such that the compliant seal is formed to the sample surface. In another embodiment, the i.d. of at least the skirt is larger than the perimeter of the sample, such that the compliant seal is formed to the sample holder.

In an alternate embodiment, the compliant seal is an inflatable and deflatable bladder which may be deflated for change of sample and inflated to re-establish perimeter seal around the sample. In this embodiment, the samples are presented sequentially in an x, y sliding tray or rotary platter, or R-theta platter during inflate/deflate cycles to effect an inexpensive automatic sample changer.

BRIEF DESCRIPTION OF THE DRAWINGS

The Foregoing and other aspects, benefits and advantages of the invention will be better understood from the following detailed description of preferred embodiments of the invention with reference to the drawings, in which:

FIGS. 4B-F have thus illustrated eight different optical path lengths obtainable within a single laser ablation system, simply by moving either wedge mount 125 (FIGS. 4B-E) or mirrors 31, 30.

DETAILED DESCRIPTION OF THE INVENTION

Figure 2A:
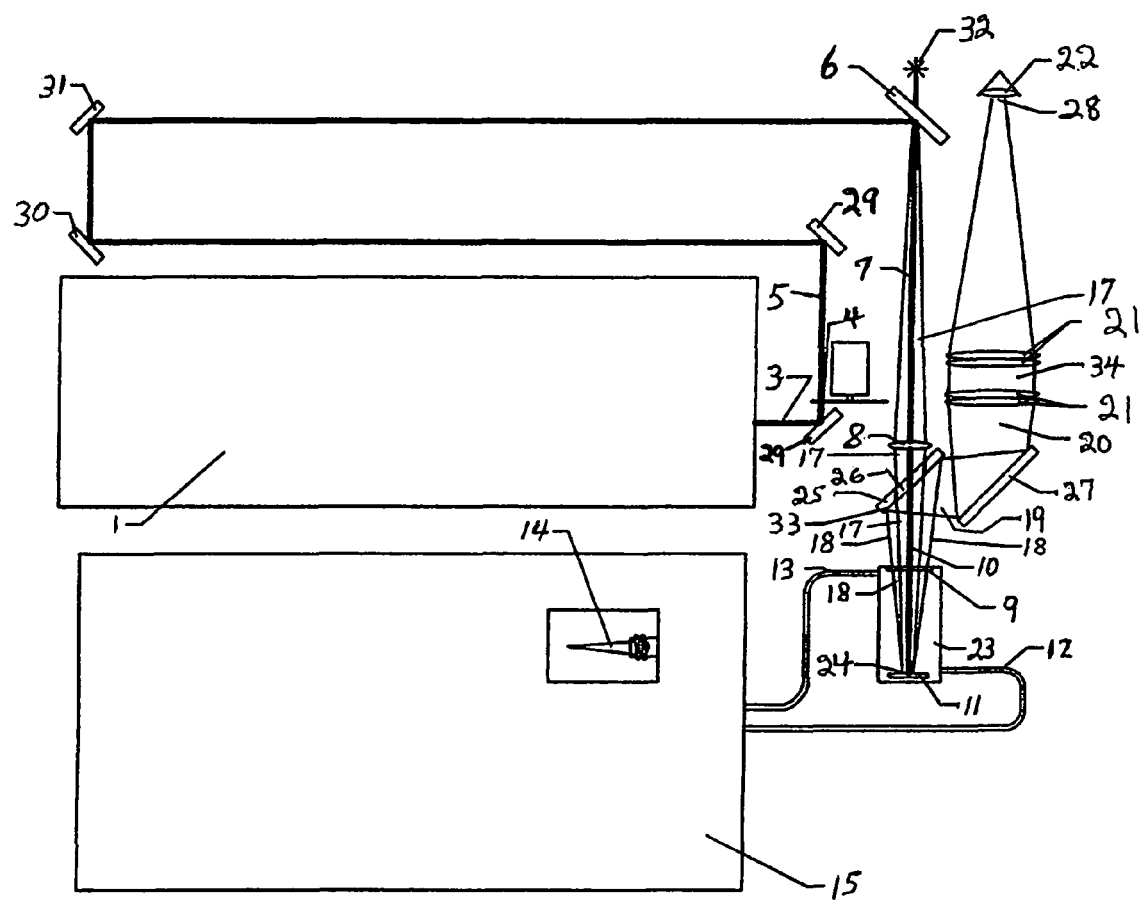
FIG. 2A is an unscaled 2-dimensional diagram of an embodiment of the invention laser ablation large laser (1), mirror-with-hole (25, 26), and long objective focal length system (8).
Figure 2B:
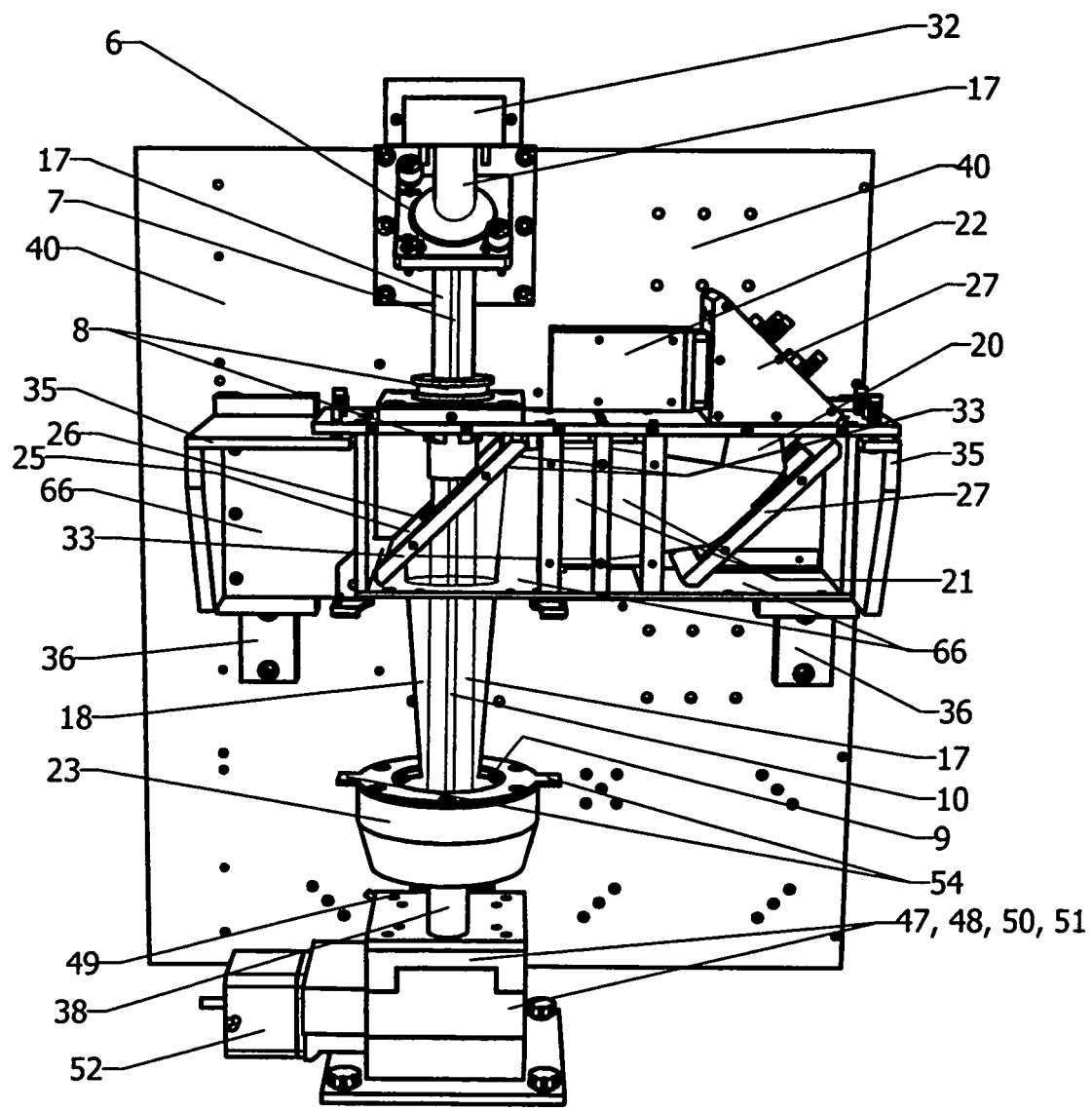
FIG. 2B is a 3-D front view (at slightly elevated vertical perspective) preferred invention embodiment drawing showing a mirror-with-hole (25, 26) and an optical gantry (35, 36, 66) containing objective lens (8), mirror-with-hole (25, 26), sample cell lift hooks (121), and achromatic white light path (33, 21, 27, 20) with camera (22). Gantry (35, 36, 66) raises and lowers to stack or unstack the stackable sample ablation cell (23) onto post ((38)—same as (81) in FIG. 10) by means of tabs (54) and lift hooks (121).

Referring to FIGS. 2A-B, a preferred embodiment of the invention involves a mirror-with-hole (25, 26) positioned below long focal length invention laser objective lens (8). The invention mirror-with-hole (25, 26) allows a focused invention UV laser beam (7, 10) to pass (unaltered) through the hole (26) to the solid material surface (11) while the invention observer (22) visible "white light view" (28) of said solid material surface is obtained off axis with the invention mirror perimeter (33) essentially concentrically surrounding the hole (26) and said UV laser beam (7, 10) passing through said hole (26). The advantage of this invention is that a final delivery segment (to the solid sample surface (11)) of the invention UV laser beam (10) is coaxially superimposed with an initial segment (18) of the invention visible "white light" observer view (22) with both invention paths sharing a single coincident focal plane (24), which is the "image" plane of the invention laser objective lens (8) and is also the "object" plane of the invention achromatic white light camera lens doublets (21), but without the two invention paths sharing any common steering or focusing optic, thus effecting optical "decoupling" of the invention UV laser beam (10) from the invention visible "white light" observer view (18, 20, 22), even though the two invention light paths coaxially share a superimposed path segment (10, 18). The focal length of invention UV laser ablation objective lens (8) is longer than conventional prior art analytical laser ablation objective lens focal lengths and the invention longer objective lens focal length creates "working room" under said invention laser objective lens (8) which allows room for the invention "mirror with hole" (25, 26) to fit in under said invention objective lens, without interfering with the invention sample ablation cell (23) or its window (9).

Invention optical decoupling of the two paths is desirable for UV laser ablation because a UV laser focusing lens ((8) if refractive, and regardless of quality) is not an ideal, aberration-free viewing optic for visible "white light" observer or camera viewing (22). Conversely, an achromatic lens (21) designed for high quality "white light" viewing by an observer (or camera (22)) is not suited to UV laser focusing (a high quality visible white light achromatic lens being typically made of glass (or plastic) and therefore opaque to UV laser light). The mirror-with-hole (25, 26) invention optically decouples the laser path (10) from the observer (or camera) path ((18, 20, 22) no shared optical steering or focusing elements), and allows completely separate (individually optimized) focusing optics (8 versus 21) to be used for each invention path, though an invention path segment (10, 18) is traversed by both invention beams, and it specifically provides a higher quality achromatic "white light" view (22) of the solid material surface before, during, and after an invention UV laser ablation event. Sharper invention white light images of the sample surface (11, 24) are therefore seen by the observer or camera (22), while a high quality invention UV laser objective lens (8) produces a high quality laser spot on the sample (11), to effect the best ablation characteristics with the invention. The best UV ablation is thus obtained by the invention, while simultaneously yielding the best quality white light view of the event.

Referring to FIG. 2A, a preferred embodiment invention excimer or SMR Nd-YAG laser (1) is substantially more powerful than corresponding lasers used in prior art analytical laser ablation. This aspect of the FIG. 2A invention analytical laser ablation invention is enabled by the unusually long focal length of invention laser objective lens (8) which has focal length greater than F=40 mm (and preferably F=150 mm or more in a nonlimiting example) and is about 4× longer focal length (in a nonlimiting example) than prior art excimer or SMR Nd-YAG analytical laser ablation, and which enables nominally 4× less demagnification and nominally 4× larger focused invention laser spot diameter (24) according to the parametric equations (using earlier defined terms):

$$1/F = 1/O + 1/I \text{ and } m^{-1} = O/I$$

With nominally 4× larger (nonlimiting example) invention excimer or SMR Nd-YAG focused spot diameter (24), the FIG. 2A preferred invention embodiment can employ a 16× larger SMR invention laser (1) without exceeding the ideal irradiance range (IIR in J/cm²/ns) of solid samples. The prior art laser ablation system of FIG. 1A cannot do this, owing to a 4× (or more) shorter focal length prior art objective lens (8) which does not facilitate focused laser spot diameters above 0.2 mm in prior art commercially available analytical laser ablation systems using excimer or SMR Nd-YAG lasers.

Further manipulation of invention object and image distances according to the above listed parametric equations would actually allow up to a 1.5 mm invention spot diameter and a 30× larger invention laser without exceeding the IIR of solid samples in a nonlimiting example. The (nonlimiting) combination of an invention 4-30× larger laser with oversized invention spot diameters in the (nonlimiting) range of 0.4-1.5 mm will yield substantially higher ablation rates at typical sample IIR's and more bulk analysis sensitivity (e.g. 4-30× more) than prior art excimer or SMR Nd-YAG analytical laser ablation system. Ultra-trace bulk solids analysis in the parts-per-billion (ppb) range may thereby be achieved by a preferred invention embodiment.

The greatest sensitivity for laser ablation analysis for a given material and a given laser size will occur with the laser operating at 100% output power and the full laser beam focused into a spot diameter yielding the ideal irradiance range (IIR) for that sample material and laser wavelength. Since sample materials vary widely in values of IIR, it would be desirable to have a wide range of full power irradiance values available for a single analytical laser ablation system. This is not possible with prior art laser ablation systems which have a fixed object distance (O). The lens formula dictates that for a fixed prior art object distance (O) and a fixed prior art focal length (F), the prior art image distance (I) and therefore the prior art demagnification ratio ($m^{-1}=O/I$) will also be fixed. With a fixed prior art demagnification value, the irradiance at 100% laser power output will not vary, and so variations in IIR for different samples may not be matched at full power with a prior art system having fixed O and fixed F (yielding fixed I and fixed $m^{-1}$). Some samples may fall into the fixed IIR of a given prior art system at full power, but many others will fall outside of their IIR, thus limiting the scope and sensitivity of prior art analysis, and the reliability of prior art calibration.

A first preferred invention embodiment shown in FIGS. 2A, 3A-C, 4A, 5 and 6, a second preferred embodiment shown in FIGS. 4B-J, and/or a third preferred embodiment combining the first and second preferred embodiments solves this problem by allowing substantial practical variation of object distance (O) by as much as a full meter or more of path length. Such a large practical variation of invention object distance (O) produces a correspondingly large variation in invention image distance (I) and invention demagnification ratio ($m^{-1}$), thus enabling the FIGS. 2A, 3A-C, 4A, 5, and 6 first preferred invention embodiment and the FIGS. 4B-J second preferred embodiment and/or a third preferred embodiment combining the first and second embodiments to serve as the first known wide range, variable demagnification ratio analytical laser ablation system, capable of ablating any solid material within its IIR, and at 100% laser power output, thus simultaneously achieving maximum sensitivity and calibration reliability for bulk analysis all materials which is possible for a given laser. To achieve the required large variation in invention object distance, the dichroic mirror pair (30, 31) may be moved right or left in the FIGS. 2A, 4A, 5 and 6 diagrams, thus shortening or lengthening the object distance in the illustrated invention folded detour path.

Figure 3A:
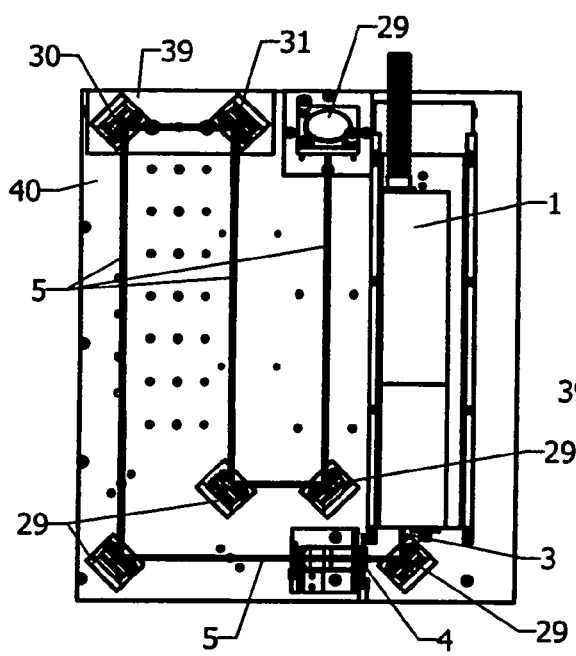
FIGS. 3A-C are rear view block diagrams of FIG. 2B front view preferred invention embodiment drawing showing invention variable laser path length (5).
Figure 3B:
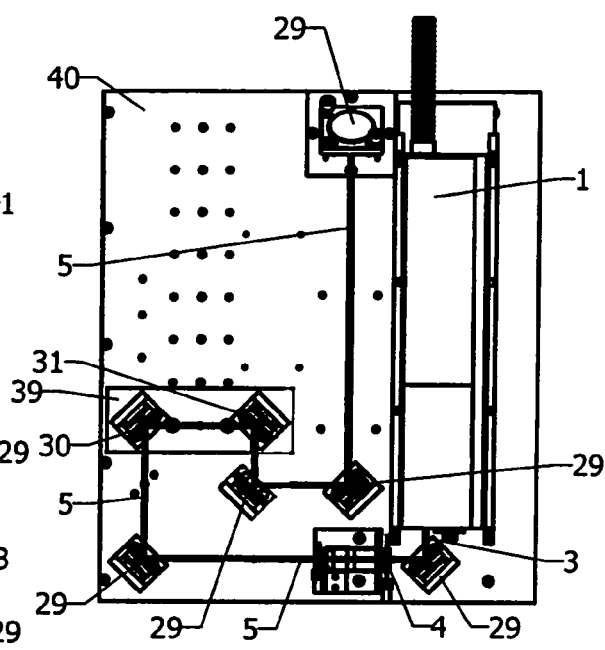
Figure 3C:
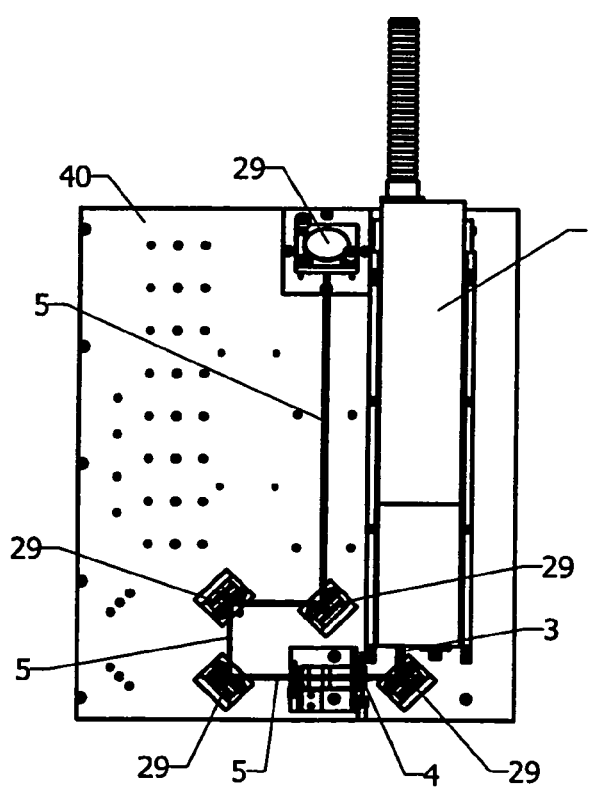
Figure 4A:
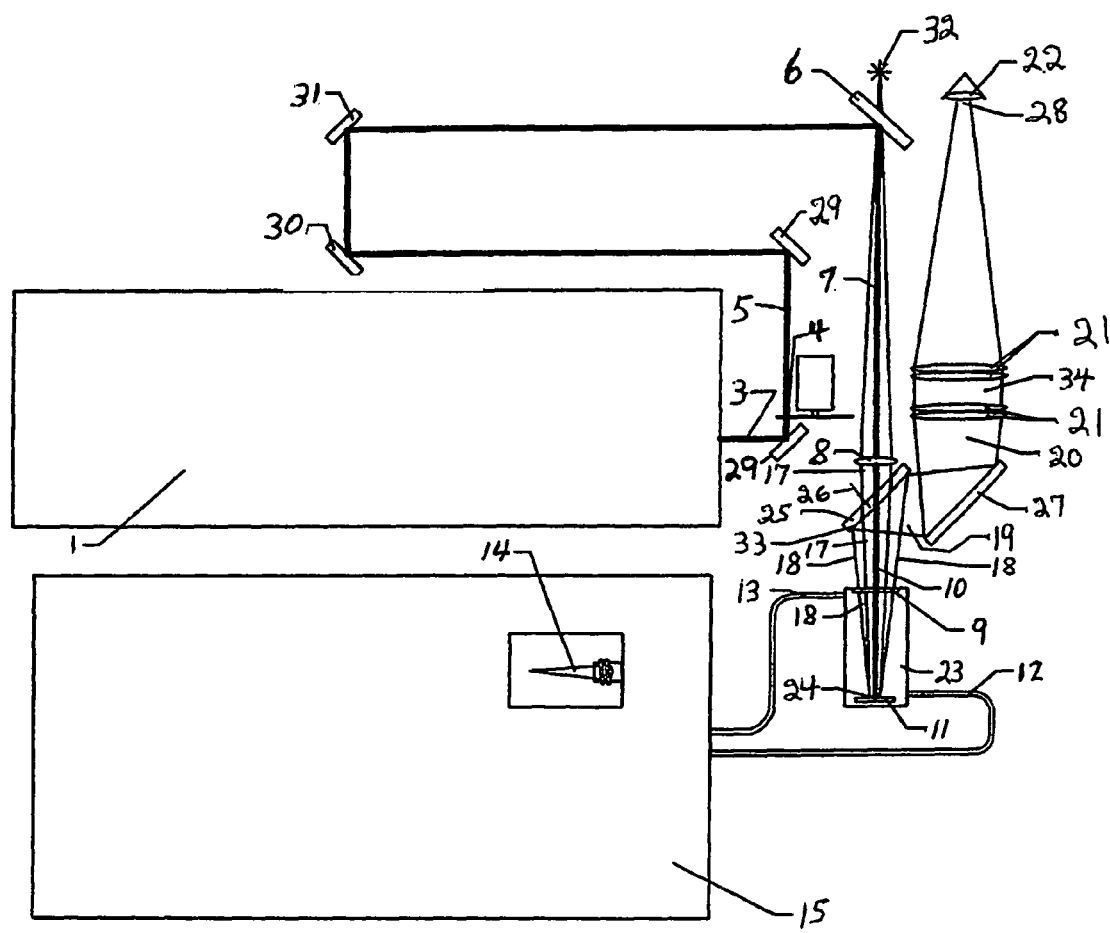
FIG. 4A is an unscaled block diagram similar to FIG. 2A, with laser path (4-7) variation by moving 2 mirrors (30-31).
Figure 4B:
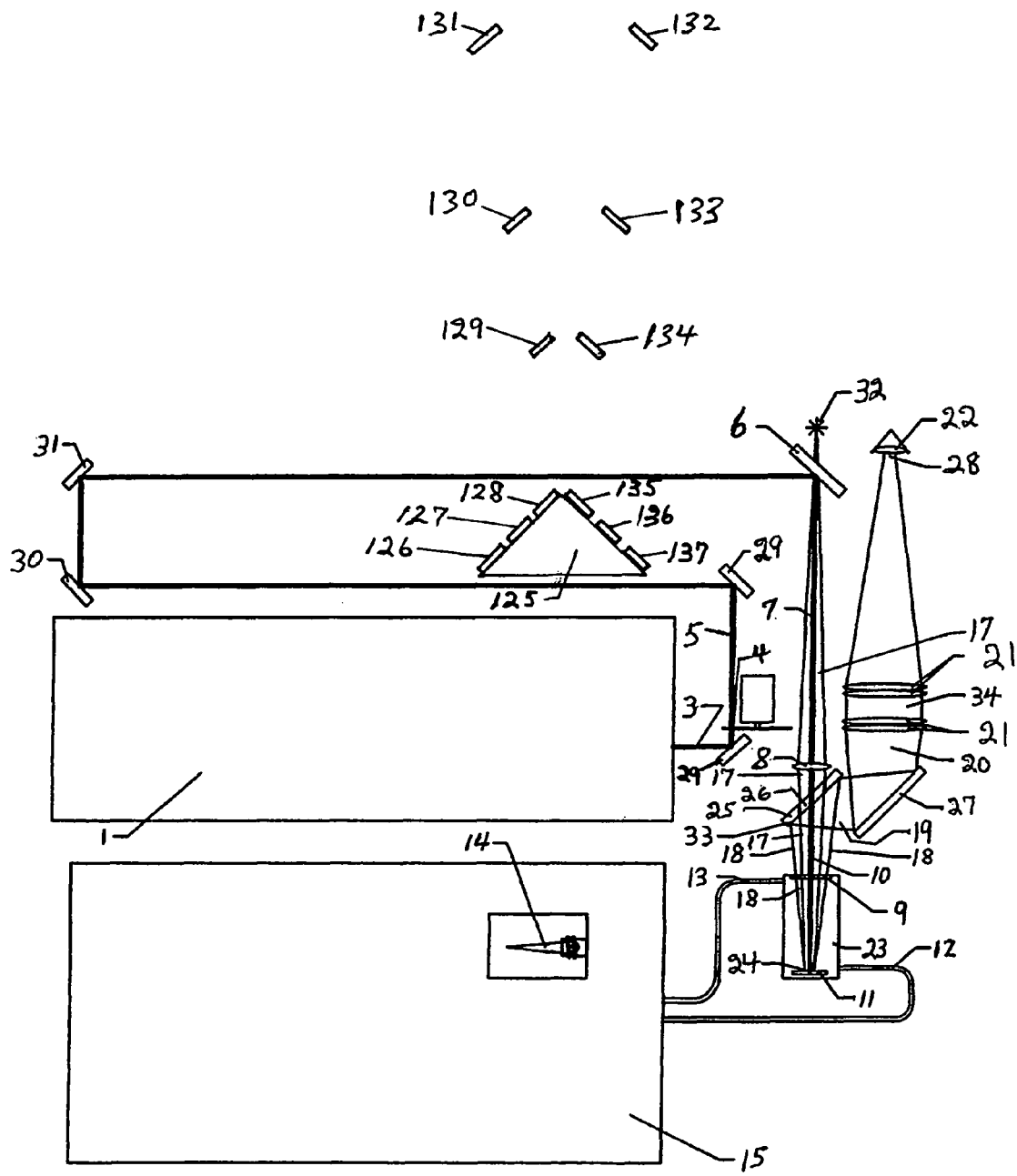
FIG. 4B is the same as FIG. 2A with addition of movable wedge mount (125) on which are is mounted six beam steering laser mirrors (126-128 and 135-137) which do not intercept the laser beam segment between 31 and 6 in this figure. Six more laser beam steering mirrors (129-134) are illustrated in fixed locations along paths at right angles to the laser beam segment between 31 and 6 in this figure. None of the twelve added laser beam steering mirrors are active in this figure and the laser beam segment length from 31 to 6 is unaffected.
Figure 4C:
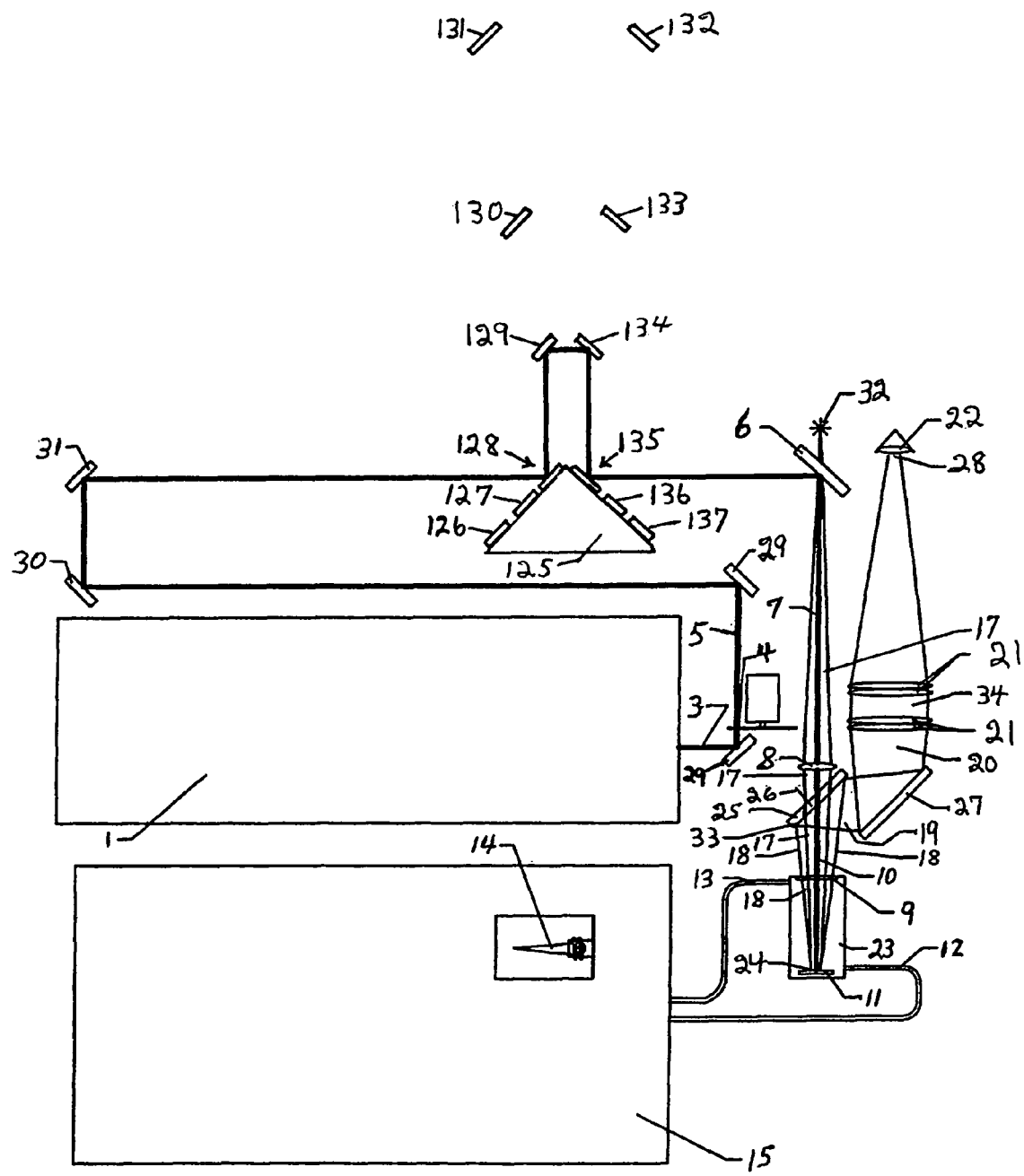
FIG. 4C is the same as FIG. 4B except for the wedge mount (125) having moved upward in the figure, inserting mirror 128 into the laser beam, which reflects the beam 90 degrees upward to mirror 129 which receives the beam and reflects it over to mirror 134 which reflects it down again to mirror 135 which restores the beam to a path coincident with its original path leading into mirror 6. The path length from 31 to 6 has been increased by an optical detour path from 128→129→34→135 with the increased path increment essentially equal to twice the offset of mirror 129 from 128, but the final laser beam segment emerging from the optical detour continues on the normal trajectory into mirror 6.
Figure 4D:
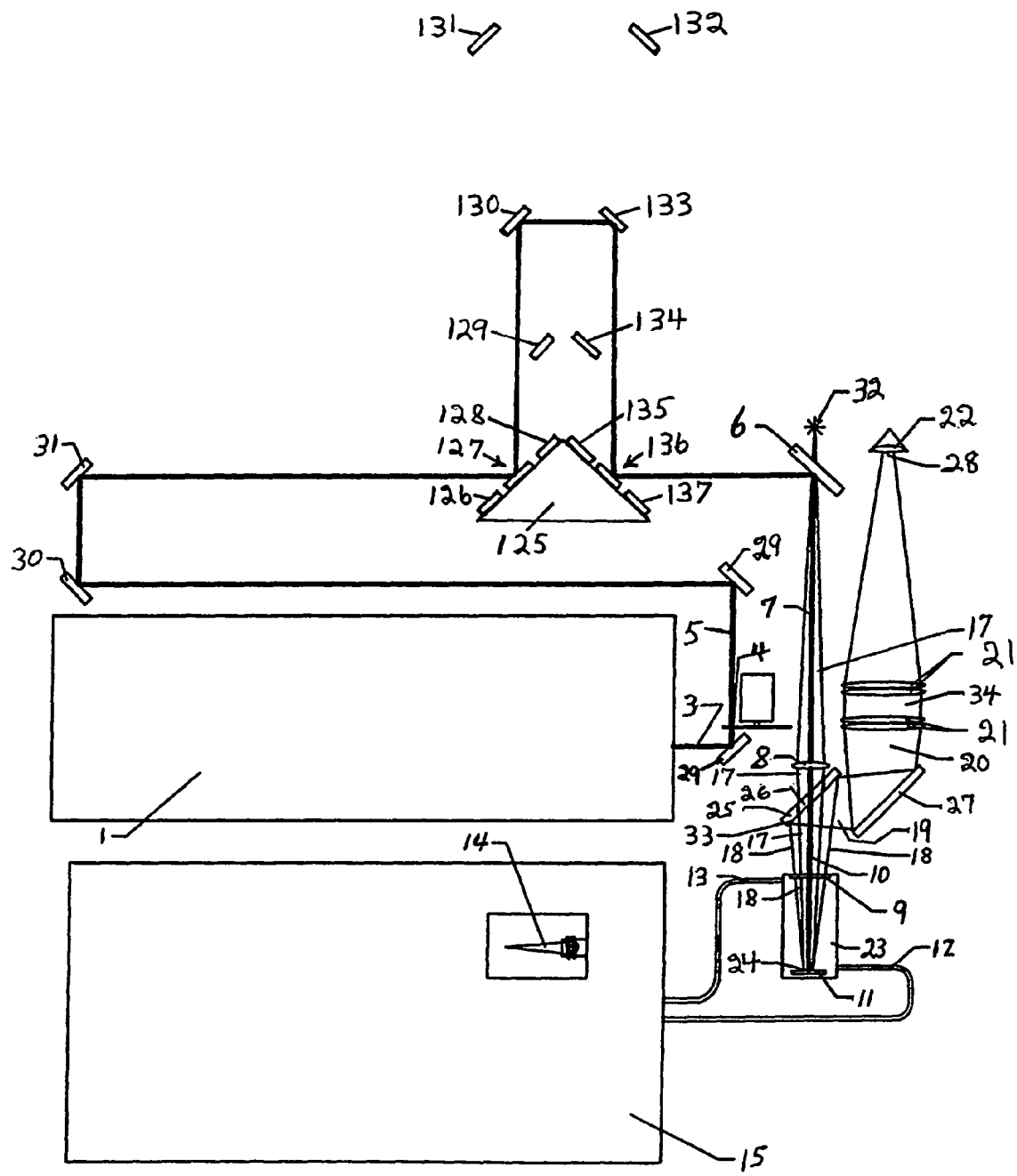
FIG. 4D is the same as FIG. 4C except for the wedge mount 125 having moved further upward in the figure, removing mirrors 128, 129, 134, and 135 from the laser beam path and replacing them in the laser beam path with mirrors 127, 130, 133, and 136 enabling a longer optical detour path from 127→130→133→136 with the optical detour path increment essentially equal to twice the offset of mirror 130 from 127, but the final laser beam segment emerging from the optical detour continues on the normal trajectory into mirror 6.
Figure 4E:
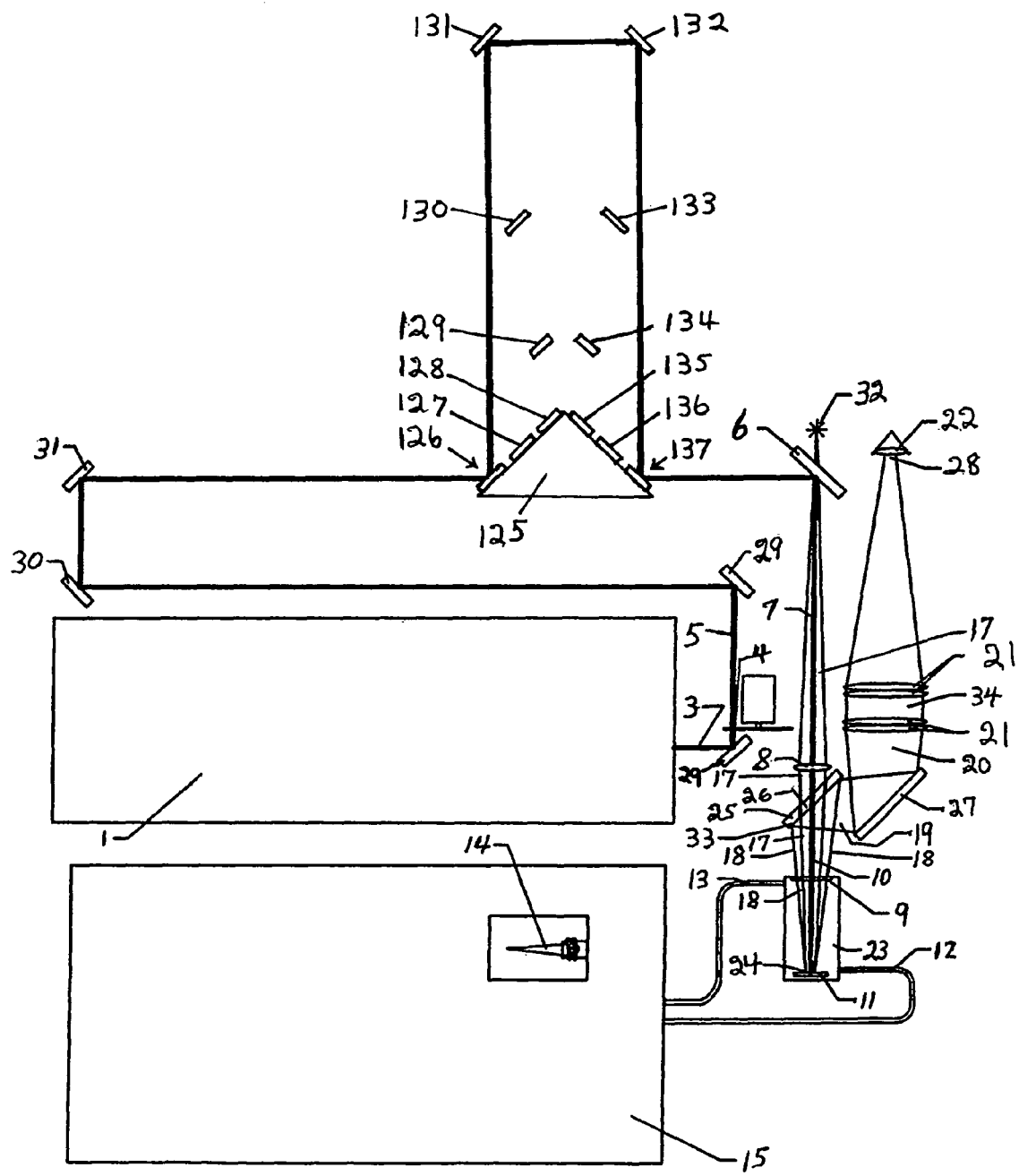
FIG. 4E is the same as FIG. 4D except for the wedge mount 125 having moved further yet upward in the figure, removing mirrors 127, 130, 133, and 136 from the laser beam path and replacing them in the laser beam path with mirrors 126, 131, 132, and 137 enabling a longer optical detour path yet from 126→131→132→137 with the optical detour path increment essentially equal to twice the offset of mirror 131 from 126, but the final laser beam segment emerging from the optical detour continues on the normal trajectory into mirror 6.
Figure 4F:
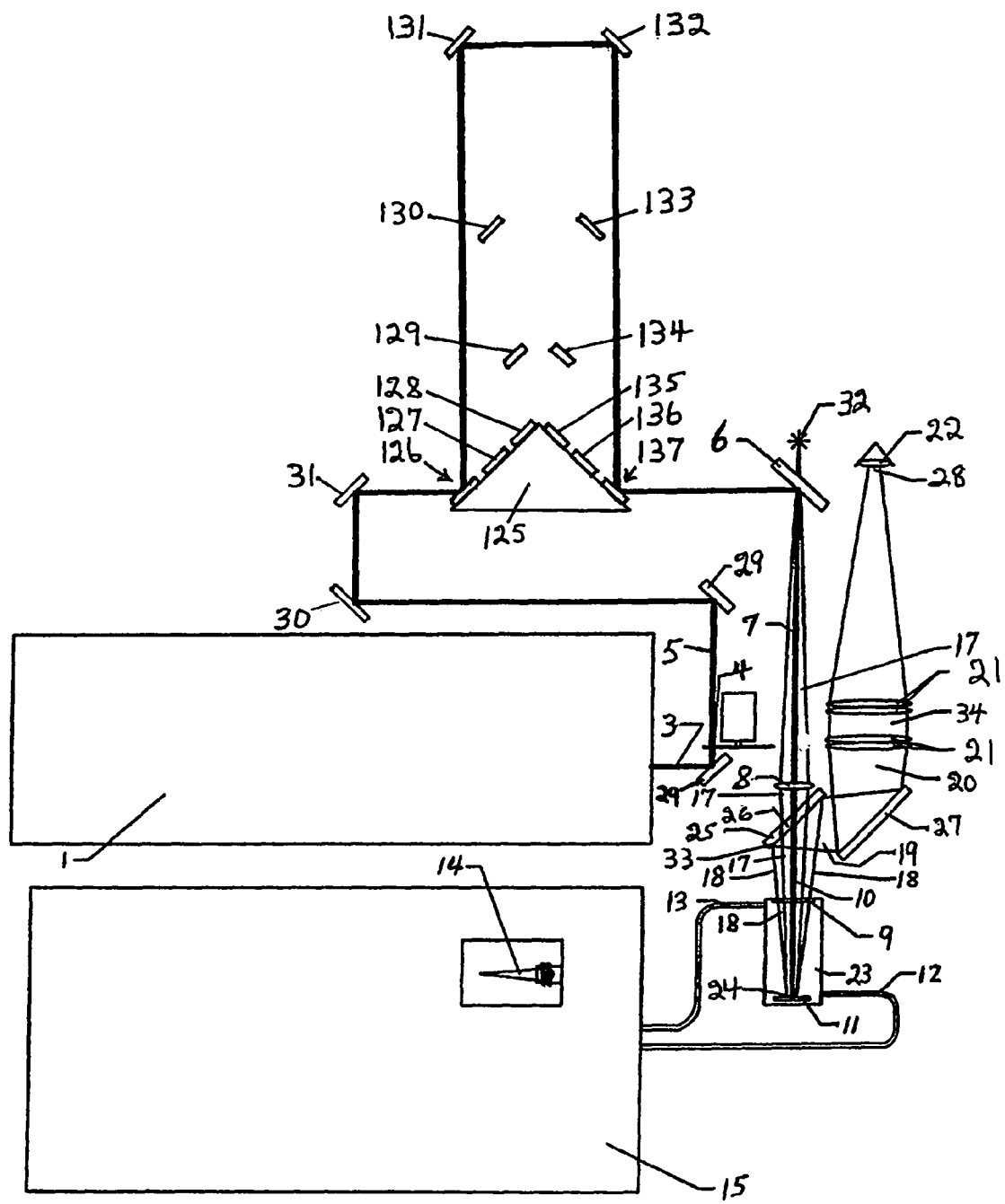
FIG. 4F is the same as FIG. 4E except that mirrors 30 and 31 have moved substantially to the right in the figure, shortening the basic optical path segment from 31 to 6 and making another four optical path lengths from 31 to 6 possible with four-position relocation of wedge mount 125 as earlier illustrated in FIGS. 4B-E but using the new positions of mirrors 31 and 32.
Figure 4G:
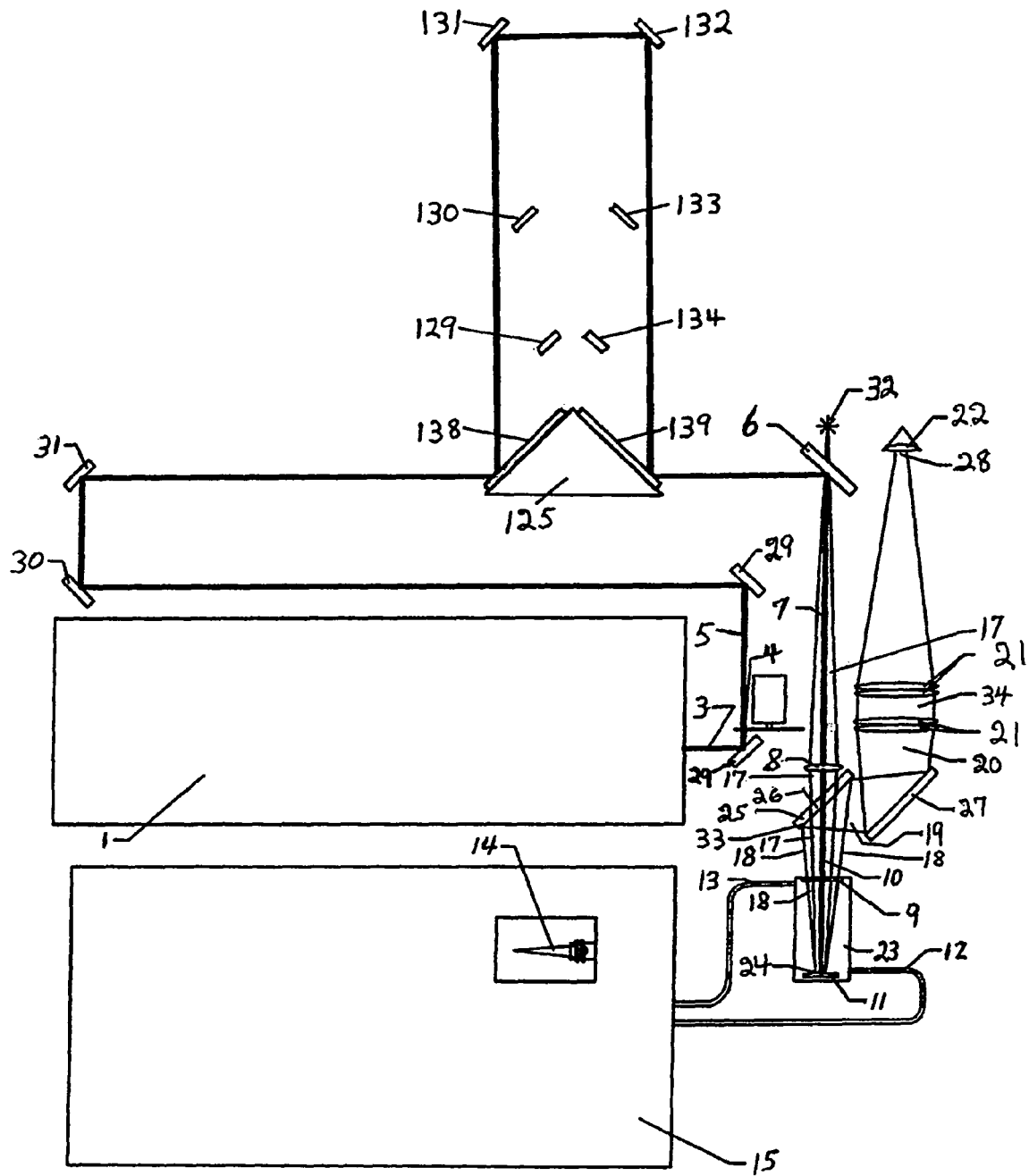
FIG. 4G is the same as FIG. 4E except that individual mirrors 126-128 have been replaced with a single larger mirror 138, and individual mirrors 135-137 have been replaced with a single larger mirror 139.
Figure 4:
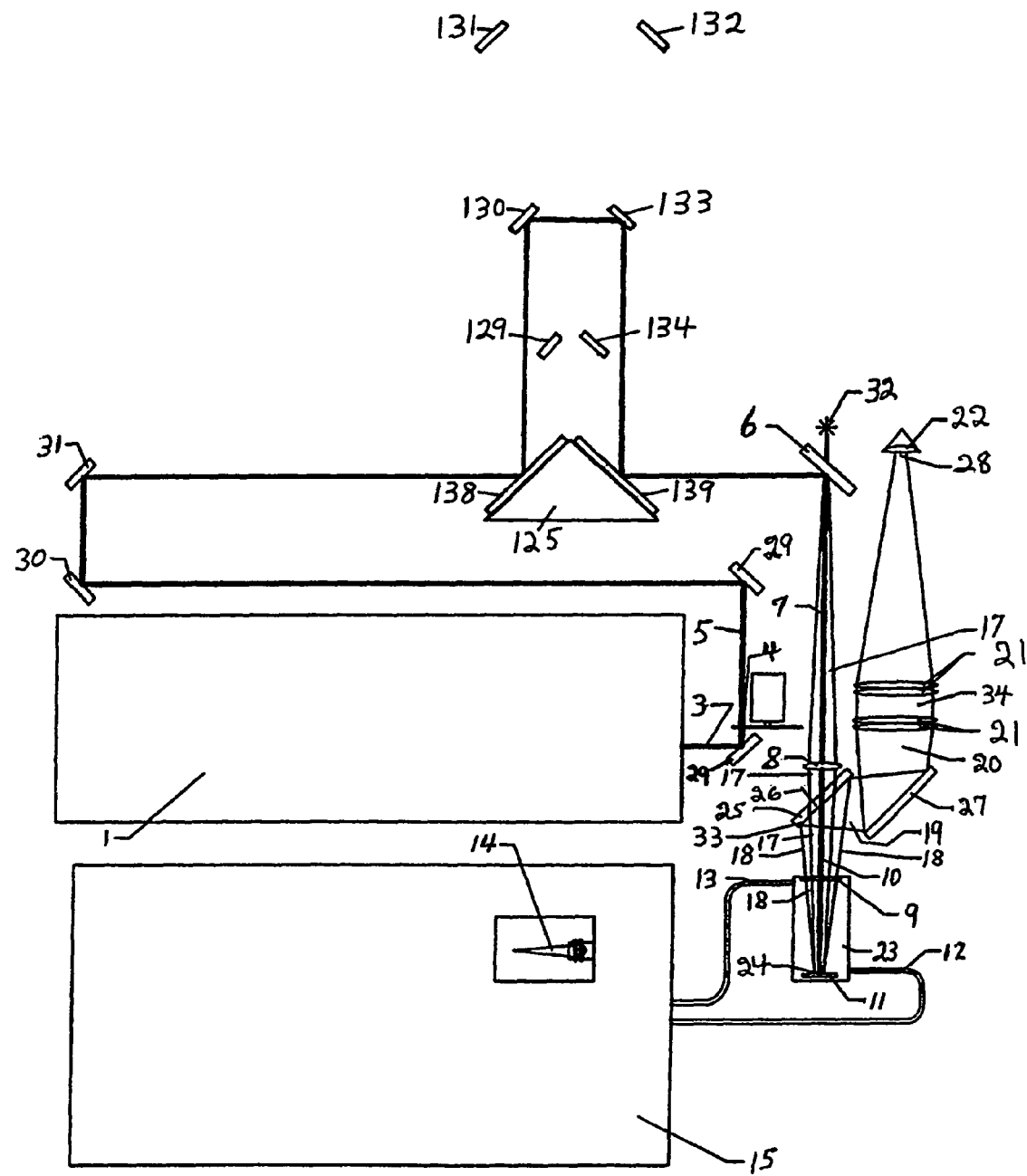
FIG. 4H is the same as FIG. 4G except that movable wedge mount has been relocated somewhat lower in the figure so that the incident laser beam (from 31) intercepts mirror 138 at a different location on the mirror, causing it to reflect to mirrors 130, 133, and 139 instead of mirrors 131, 132, and 139. The FIG. 4H optical detour path has been decreased accordingly from what it was in FIG. 4G.
FIG. 4I is the same as FIG. 4H except that movable wedge mount has been relocated somewhat lower yet in the figure so that the incident laser beam (from 31) intercepts mirror 138 at a different location yet on the mirror, causing it to reflect to mirrors 129, 134, and 139 instead of mirrors 130, 133, and 139. The FIG. 4I optical detour path has been decreased accordingly from what it was in FIG. 4H.
FIG. 4J is the same as FIG. 4I except that movable wedge mount has been relocated even lower yet in the figure so that the incident laser beam (from 31) no longer encounters an optical detour path and it proceeds without detour to mirror 6.
Figure 4:
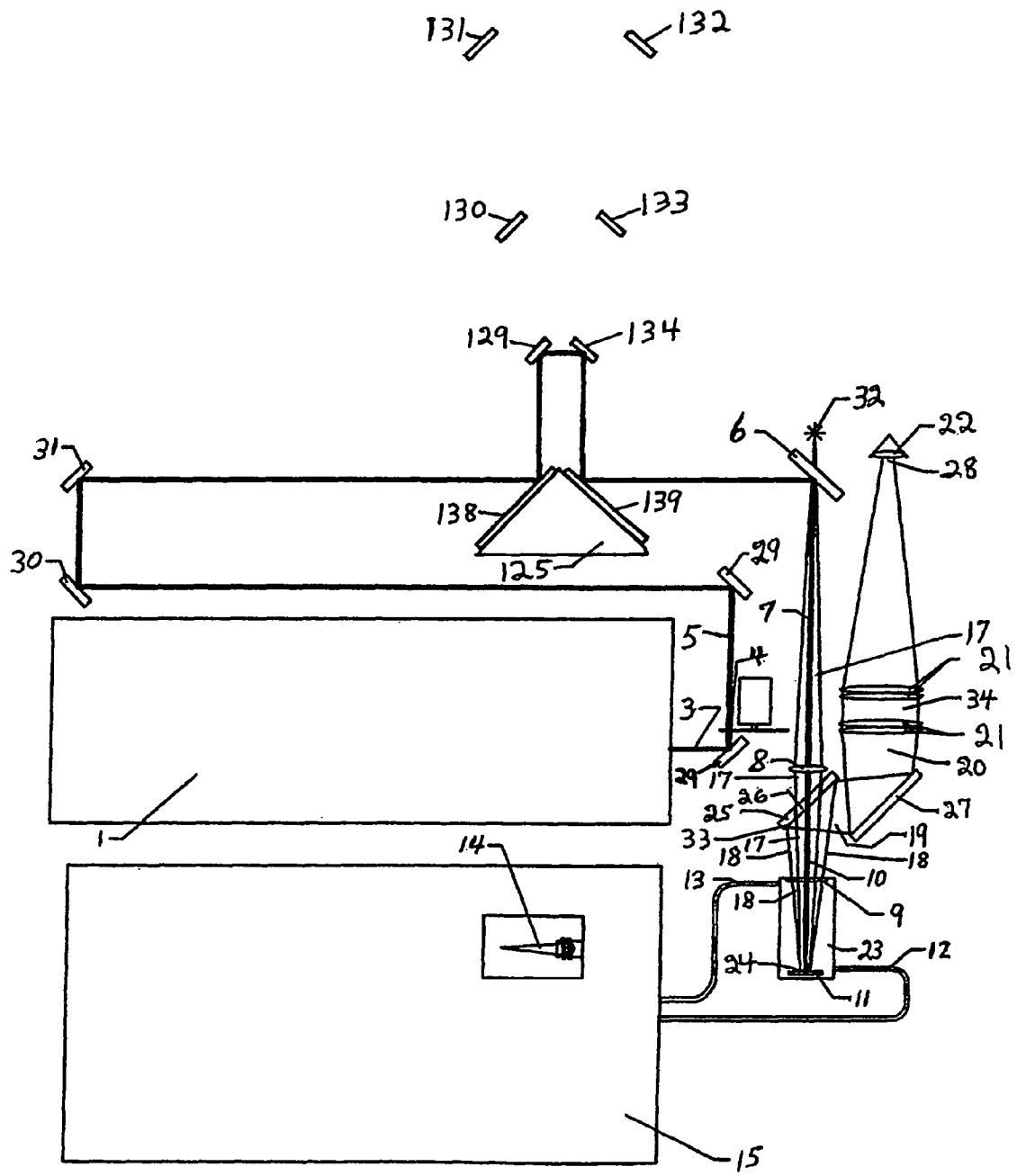
Figure 4J:
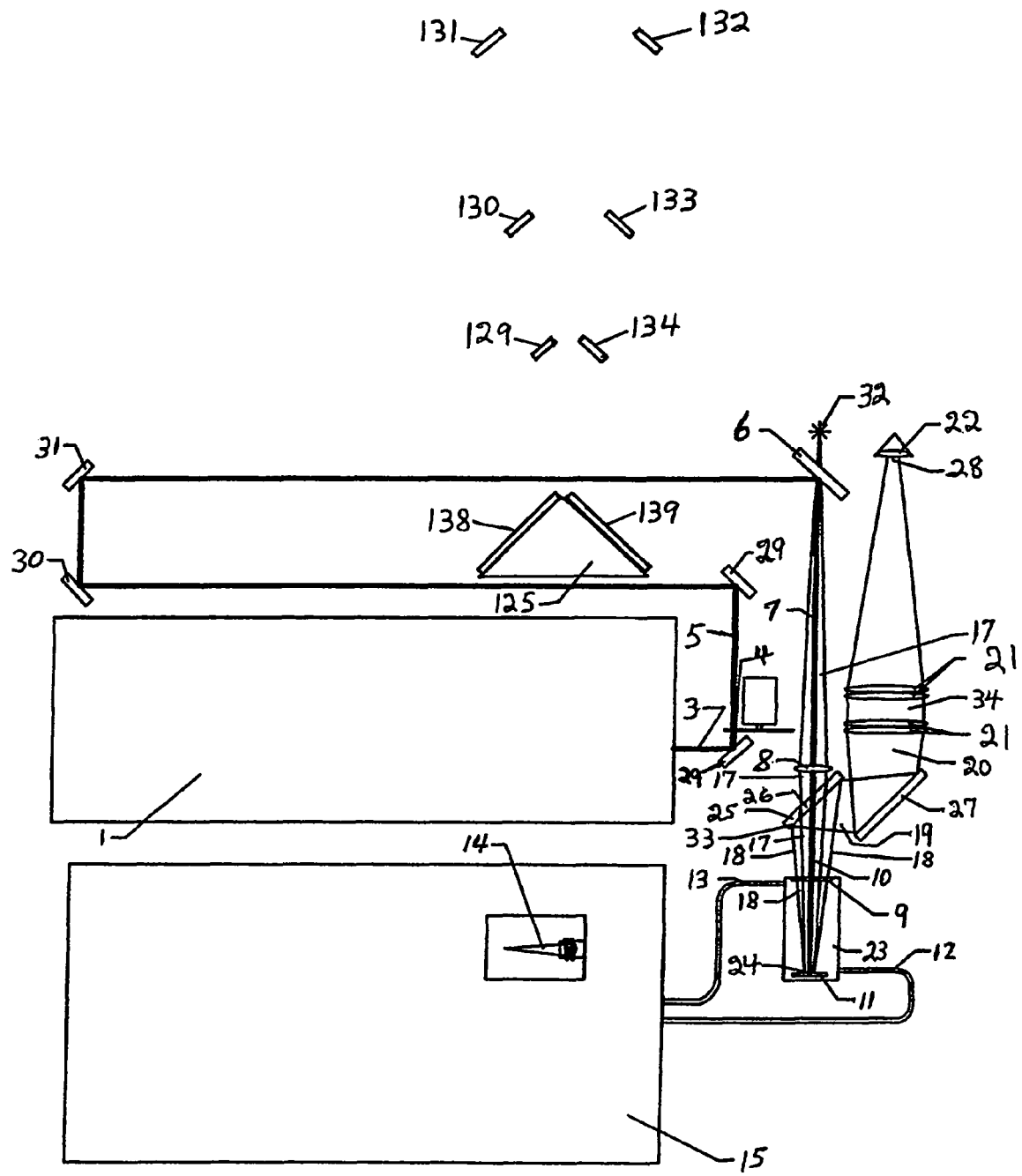
Figure 5:
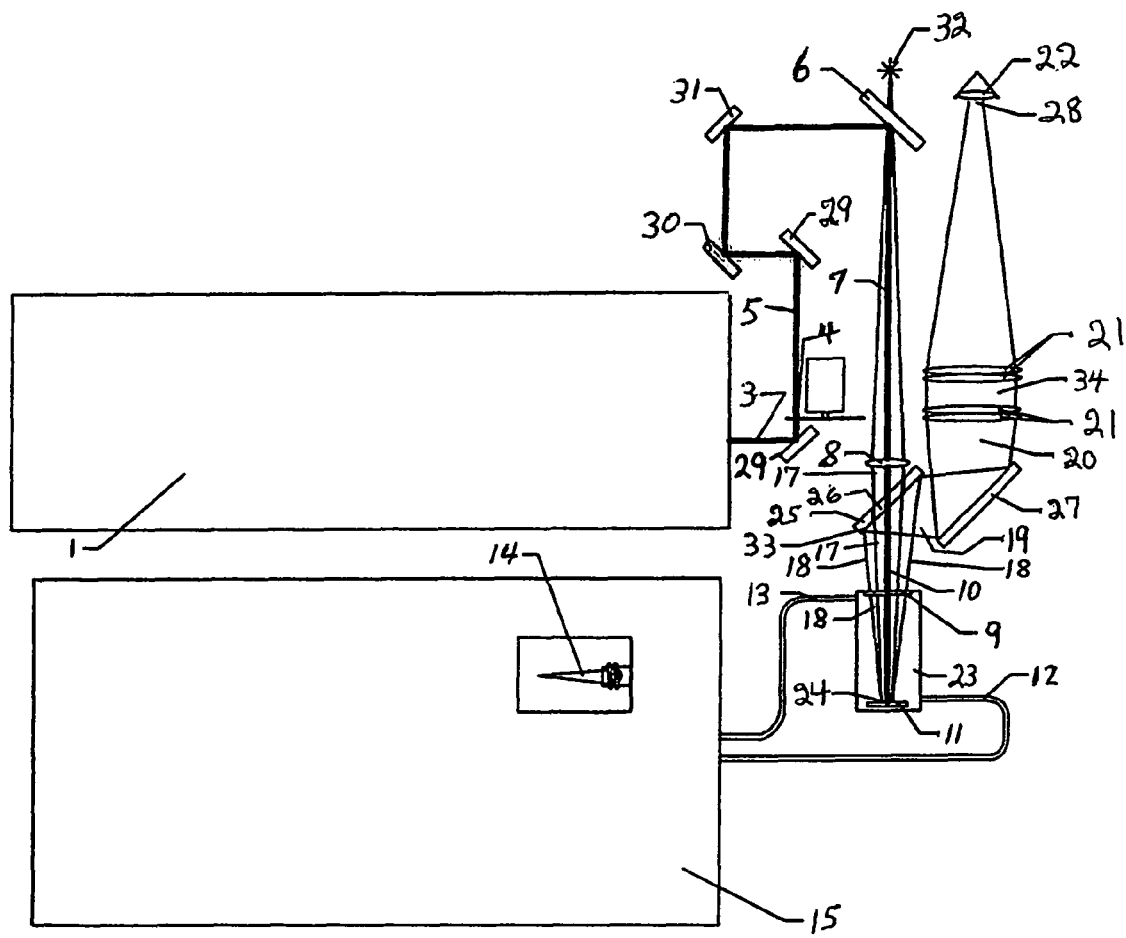
FIG. 5 is the same as FIG. 4A, but with greater movement of the mirror pair 30, 31 and shorter overall optical path length.

It has been noted that movement of laser steering mirrors 30, 31 in a direction parallel to the beam path from 29-30 in FIGS. 3A-C and in FIGS. 2A, 4A, and 5. In a second embodiment which may function alone, or in combination with parallel movement of mirrors 30, 31, FIGS. 4B-J illustrate that at least one folded optical detour path may be created which is perpendicular to the original FIG. 2A laser path segment between 31 and 6. By inserting various mirrors 126-128 with a perpendicular motion of wedge mount 125, various folded optical detour paths including 128→129→134→135 (FIG. 4C), 127→130→133→136 (FIG. 4D), and 126→131→132→137 (FIG. 4E) are enabled which lengthen the path segment between 31 and 6 by varied optical detour amounts, while still directing it coincidentally (coaxially) with path 7 through the objective focusing optic 8 focusing (with demagnification) to solid target sample 11. In a third embodiment, FIGS. 4G-J illustrate that a pair of single larger mirrors 138, 139 can replace the illustrated six individual mirrors 126-128 and 135-137 on the movable wedge mount 125 and accomplish essentially the same set of optical detour path elongations.

In summary, to achieve the required large variation in invention object distance, the dichroic mirror pair (30, 31) may be moved right or left in the FIGS. 2A, 4A, 5 and 6 diagrams, thus shortening or lengthening the object distance in the illustrated invention folded detour path. Alternatively the movable wedge mount (125) may be moved up or down in the FIGS. 4B-J diagrams, or a combination of right/left movement of the dichroic mirror pair (30-31) and the up/down movement of the movable wedge (125) may be employed.

A corresponding vertical relocation of invention objective lens (8) and/or the solid target sample 11 is needed to satisfy the lens formula ($1/F=1/O+1/I$) and keep the laser spot image (24) focused at sample surface (11). Invention mirrors (30, 31) and objective lens (8) are thus positioned to maintain a focused laser spot image (24) (of aperture 4) on the sample surface (11). In a preferred invention embodiment, the mirrors (30, 31) and objective lens (8) are moved in such a way that the lens formula ($1/F=1/O+1/I$) is always kept satisfied as the focal plane (24) remains fixed. The demagnification ratio ($m^{-1}=O/I$) and the irradiance are however greatly altered with these invention mirror and lens movements, and a wide variety of sample IIR may thereby be ideally matched by the invention.

It should be noted that vertical motion of lens 8 on a precision motion stage may or may not require invention laser system realignment, however motion of the mirror pair 30, 31 will most certainly require invention laser system realignment to keep the focused laser spot (24) exactly centered on sample position (11), taken as a reference position.

To achieve operational invention laser system realignment upon substantial relocation of mirrors (30, 31), they may be mounted on a plate (39) and plate (39) may be kinematically mounted to the invention optical platform (40). Pre-alignment of invention mirrors (30, 31) for a given plate (39) position on the invention optical platform (40) will then assure that overall invention alignment is maintained whenever plate (39) is in the given pre-aligned optical platform (40) position. A key feature of this preferred invention embodiment is that a given plate (39) is only used in one position, so each time it is installed in the one position, its kinematic mount ensures that the pre-aligned mirror (30, 31) condition is maintained. To change plate positions (relocation), a different invention plate with a separate invention mirror pair must then be substituted, with the new mirror pair being pre-aligned for the new plate position (also kinematically mounted to the new position). Essentially, this embodiment of the invention uses a new pre-aligned mirror pair and kinematically mounted plate for each available mirror position. To operationally relocate the mirrors, a new mirror pair (and plate) is selected for each position, with each separate mirror pair having been pre-aligned to its own location on the optical platform (40). The required number of mirror pairs must equal the required number of different mirror positions. Operational relocation is achieved simply by demounting the previous mirror pair (and plate) from its quick-release kinematic mount, selecting a new mirror pair (pre-aligned for the new position), and quickly clamping it into its designated (new) position. The pre-alignment characteristic of the newly selected mirror pair makes it unnecessary to re-align the system upon installation of the new pair. An alternate embodiment would have each prealigned mirror of the selected pair on separate kinematic mounts instead of on plate (39).

Figure 6:
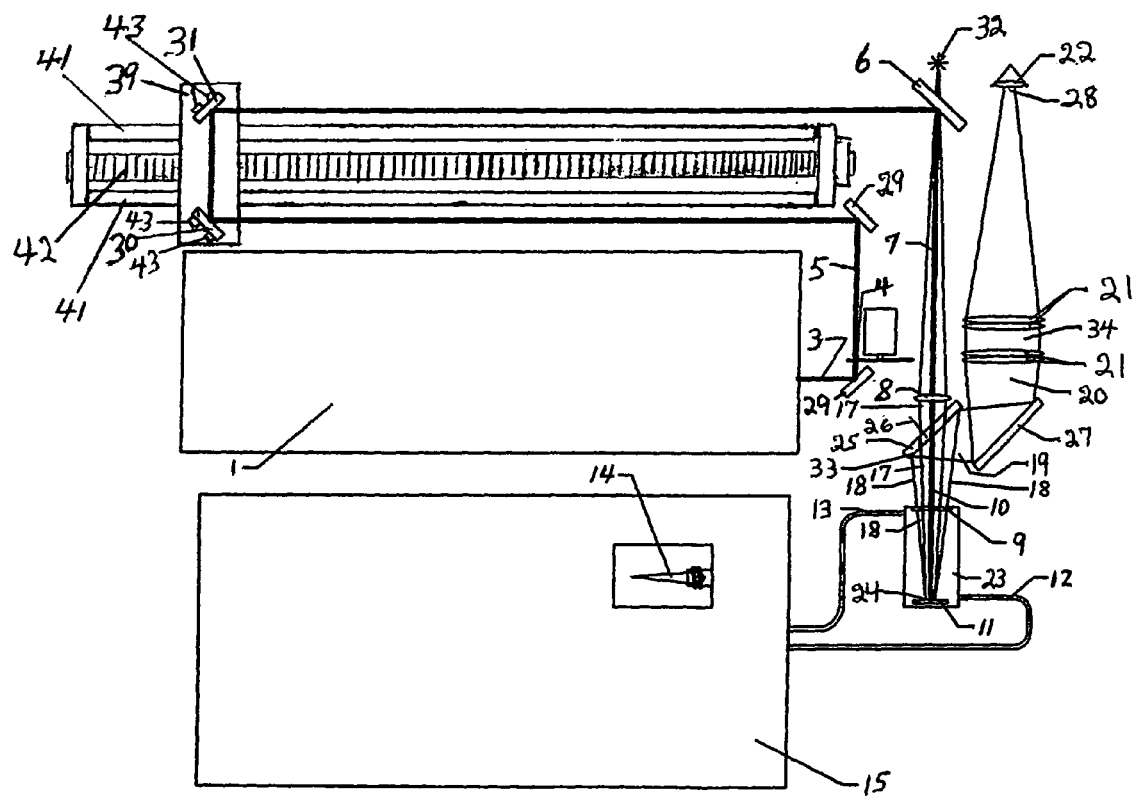
FIG. 6 is a motorized version of FIGS. 2A, 4A, and 5.

A preferred embodiment of the invention involves actual relocation of the same mirror pair 30, 31 to one or more preset locations along a precision linear track (FIG. 6). Precision micrometer settings on the gimbaling mirror angle adjustments (43) of one or both of the two mirrors may be predetermined to maintain overall system alignment for each preset location on the linear track. Pre-determination of mirror gimbal micrometer settings would be done in a preliminary setup alignment exercise performed for each preset location on the track. Once a full set of micrometer settings has been determined (separate settings for each preset track location), then those micrometer settings simply have to be replicated (for that track position) each time the mirror pair is moved to a new location. This may be done manually with precision micrometer settings, or digital stepping motors may be attached to the gimbaling adjustments and then the predetermined stepper motor addresses set for the gimbaling adjustments on the mirrors corresponding to a given track location selected. Separate stepper motor addresses (mirror gimbaling adjustments) would be predetermined for each preset track location.

In a preferred embodiment, a computer may store these stepper motor addresses and then recall them (and reload them to the stepper motors) each time the mirror pair is moved between preset locations.

Invention mirror pair motion to any location between two preset locations on the linear track may be dealt with by computer interpolation between the gimbaling stepper motor addresses for the bracketing preset locations. In this way a full range of continuously variable demagnification ratios may be operationally obtained with automatic system realignment. An invention operator need only enter the desired magnification ratio into the system computer and a digital stepping motor will automatically relocate the mirror pair along the linear track and additional stepping motors will automatically realign the mirrors to a preset or interpolated alignment corresponding to the selected track position.

In addition, the invention laser objective lens (8) may be positioned on a focus track and controlled by the computer to keep the lens formula (1/F=1/O+1/I) satisfied (image focused) for a fixed sample position, as the mirrors move. Essentially, when a new demagnification ratio is specified by the invention user, the computer will solve the parametric equations (1/F=1/O+1/I and $m^{-1}$=O/I) for a fixed value of F and the specified $m^{-1}$ to yield corresponding values of O and I which determine the mirror (30, 31) and lens (8) placements for that $m^{-1}$. Then the computer will look up (or interpolate) new pre-determined pre-alignment values of mirror gimbaling (angle) adjustments (43) to restore system alignment. This invention feature is completely new to analytical laser ablation and it will facilitate operational selection of a wide variety of demagnification ratios to meet the application-specific IIR requirements of virtually any solid sample, while allowing the full available laser power to be used for each analysis. This will maximize invention sensitivity and also maximize overall analytical instrument calibration precision, accuracy, consistency, and reliability.

Path length variation by the folded path detours of FIGS. 4B-J have the special benefit of having fixed, pre-aligned mirror settings on a precision gimbaling mount for each mirror in the series 129-134 which automatically maintain alignment of image 24 at a preselected reference location on sample 11 as wedge 125 is relocated to its various positions which are preferred to be kinematically stabilized at each location. Kinematic stabilization ensures that wedge 125 is consistent in its locations, such that the fixed, pre-aligned, preset mirrors 129-134 always ensure that image 24 remains centered at the preselected reference location on sample 11 as wedge 125 is relocated.

A further preferred embodiment to extend the range of usable spot diameters and demagnification ratios would include variable focal length in the invention objective lens. To facilitate this, interchangeable invention objective lenses of varying focal length may be employed, including (in one preferred embodiment) a rotary turret containing at least two invention objective lenses of different focal length. Invention zoom laser objective lenses and variable focus laser objective lenses may also be envisioned in other embodiments, either alone, or in combination with other lenses (individually interchangeable or on a turret) so long as they have the requisite UV transmission properties.

In one preferred embodiment, the invention objective lens (or turret) may be mounted on a precision motion stage for repositioning (as invention mirrors are relocated). In another embodiment, the invention objective lens (8), mirror-with-hole (25, 26), and visible "white light" achromatic lens (21) and camera (22) may all be mounted on a FIG. 2B gantry, such that the entire gantry (66, 35, 36) moves to reposition these optics, as invention laser mirrors (30, 31) are relocated as in FIGS. 2A, 3A-C, and FIGS. 4A, 5 and 6 and/or as the movable wedge mount (125) is relocated as in FIGS. 4B-J.

In one preferred embodiment, the invention gantry may also be precisely moved (up and down) to focus the laser spot image and camera object planes (if coincident) onto the solid sample surface. In another embodiment the invention camera may be relocated to shift the white light object plane to keep coincident with the laser spot image plane which may move upon invention laser mirror and laser objective lens repositioning to achieve varied invention demagnification ratios.

In another preferred embodiment, the solid sample (11) and/or sample ablation cell (23) may be moved on a precision vertical motion stage to achieve focus of the laser spot image (24) and camera object planes (28) to the sample surface (11).

Invention modularity may accommodate lasers of widely differing size and power on a single "flex" platform, without repositioning or reconfiguring the remaining optics.

Figure 1A:
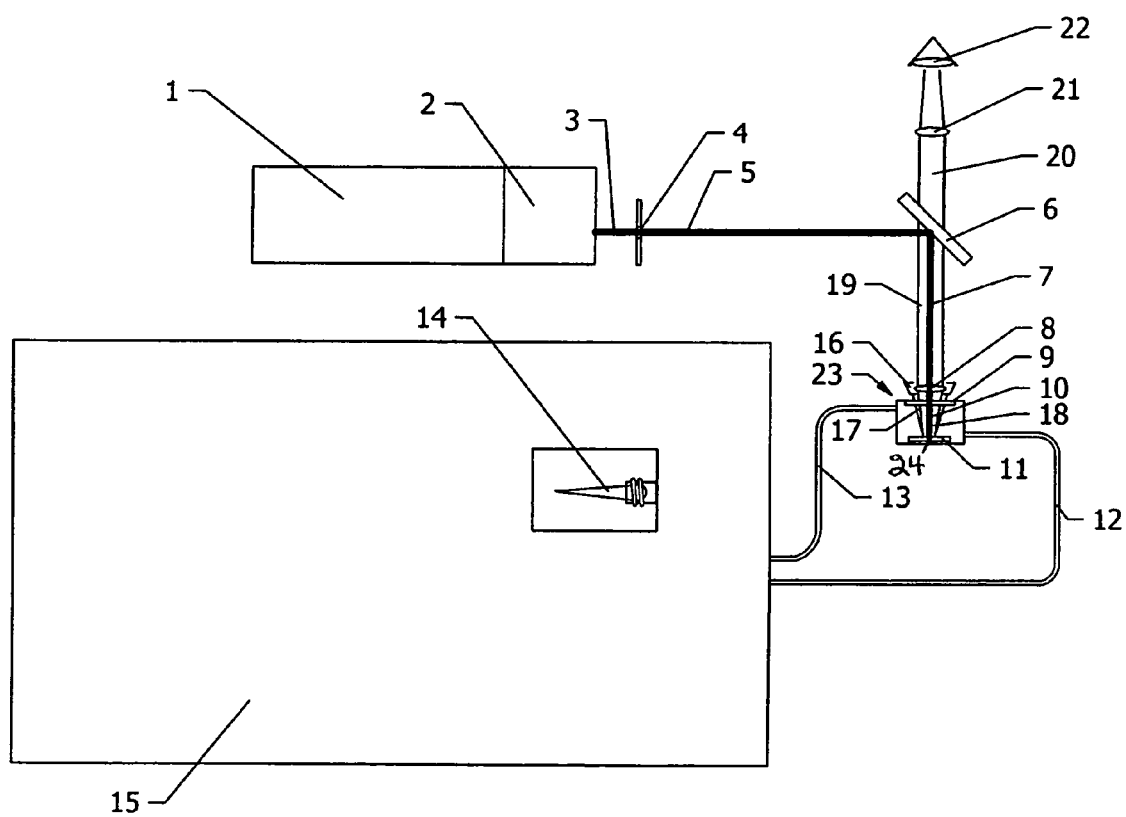
FIG. 1A is an unscaled 2-dimensional block diagram of a prior art analytical laser ablation system.
Figure 1B:
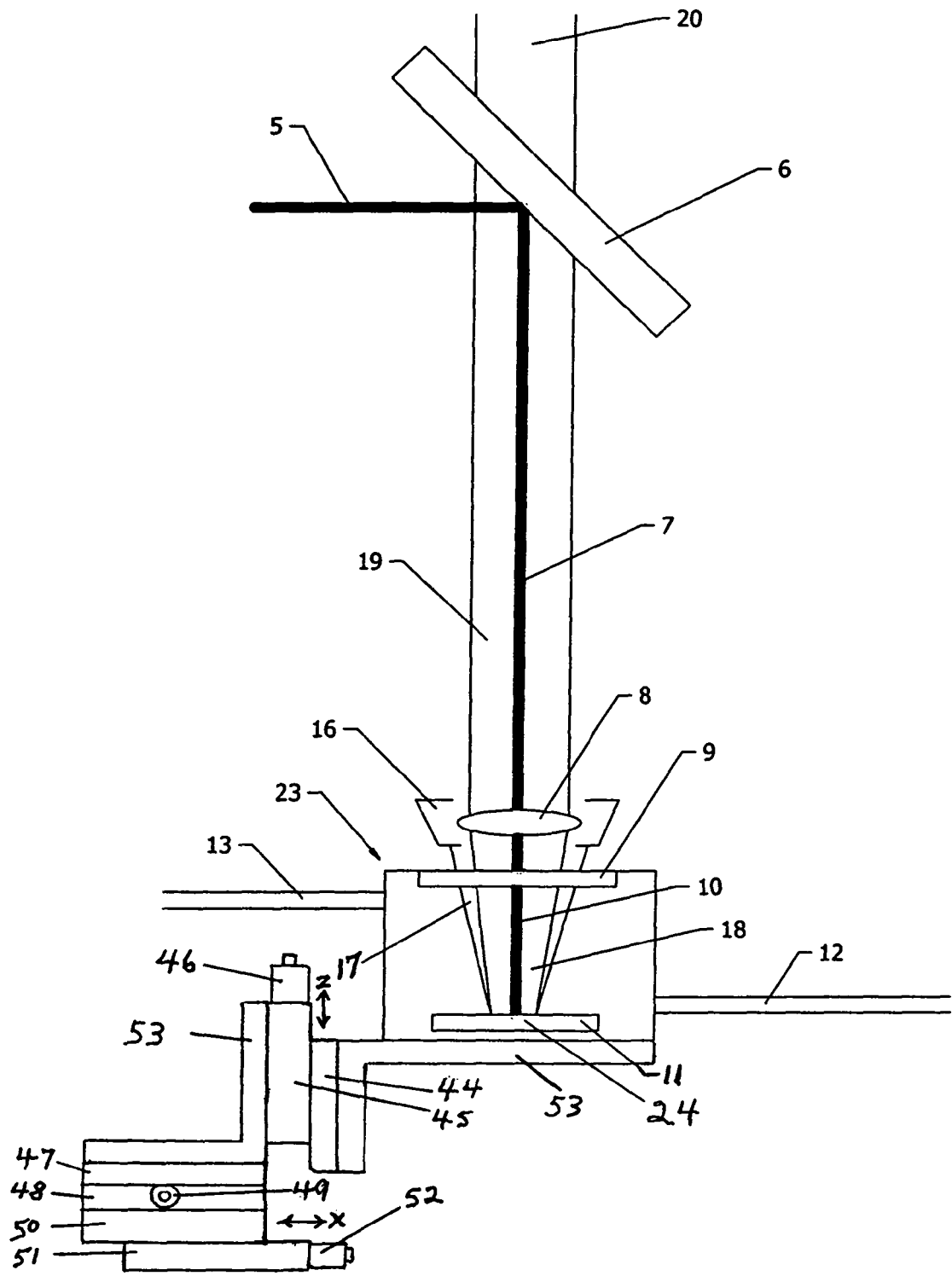
FIG. 1B. is a truncated block diagram section of FIG. 1A, enlarged to show greater detail and a clearer view of prior art items 8-13, 16-19, 23 and 24 which appear in both figures, with addition of a set of X,Y, Z motorized translational stages (44-53).
Figure 7A:
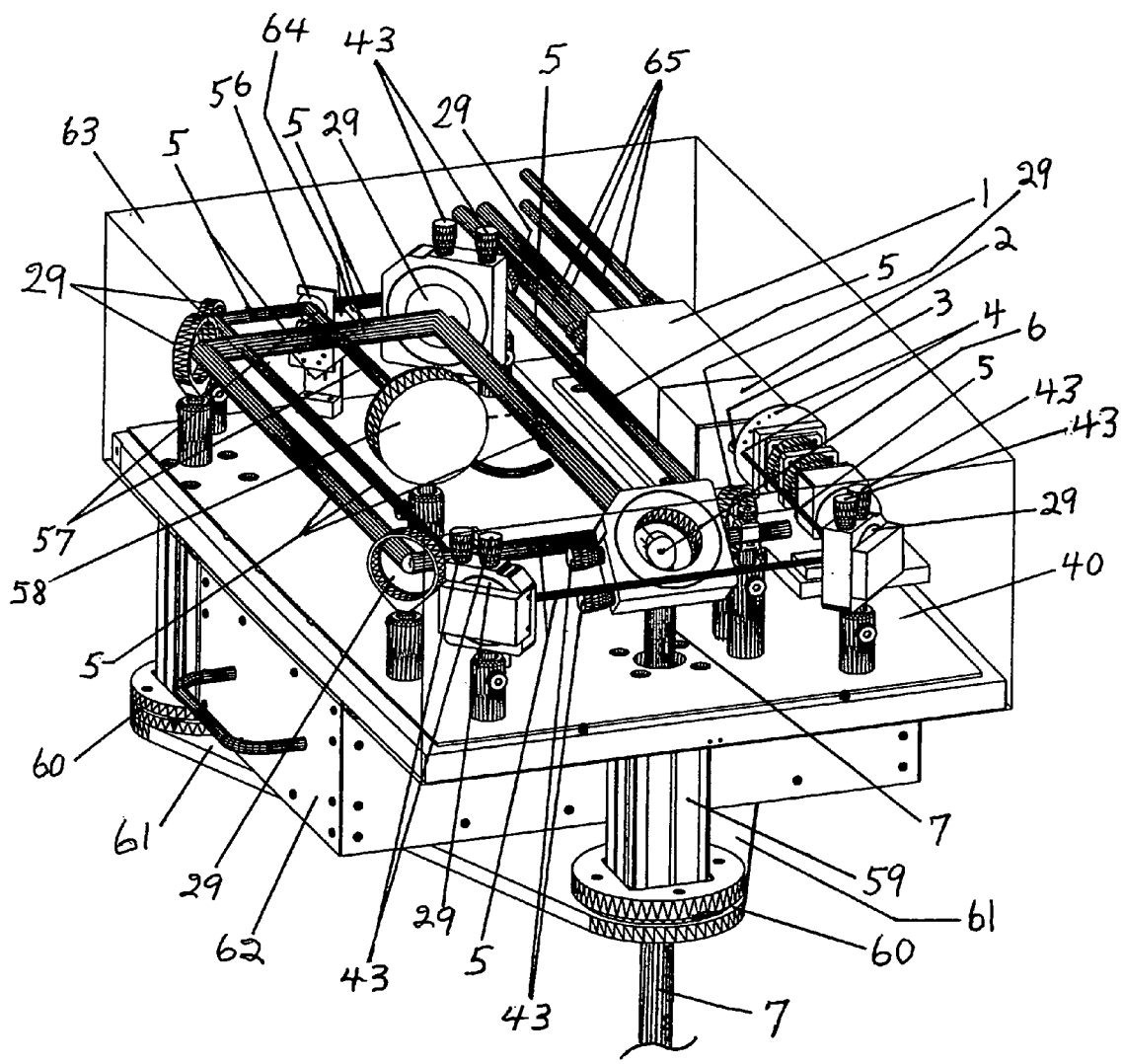
FIG. 7A is a 3-D angled perspective view of an upper module (outside of radiation hot cell) of a rad-hardened laser ablation invention.
Figure 7B:
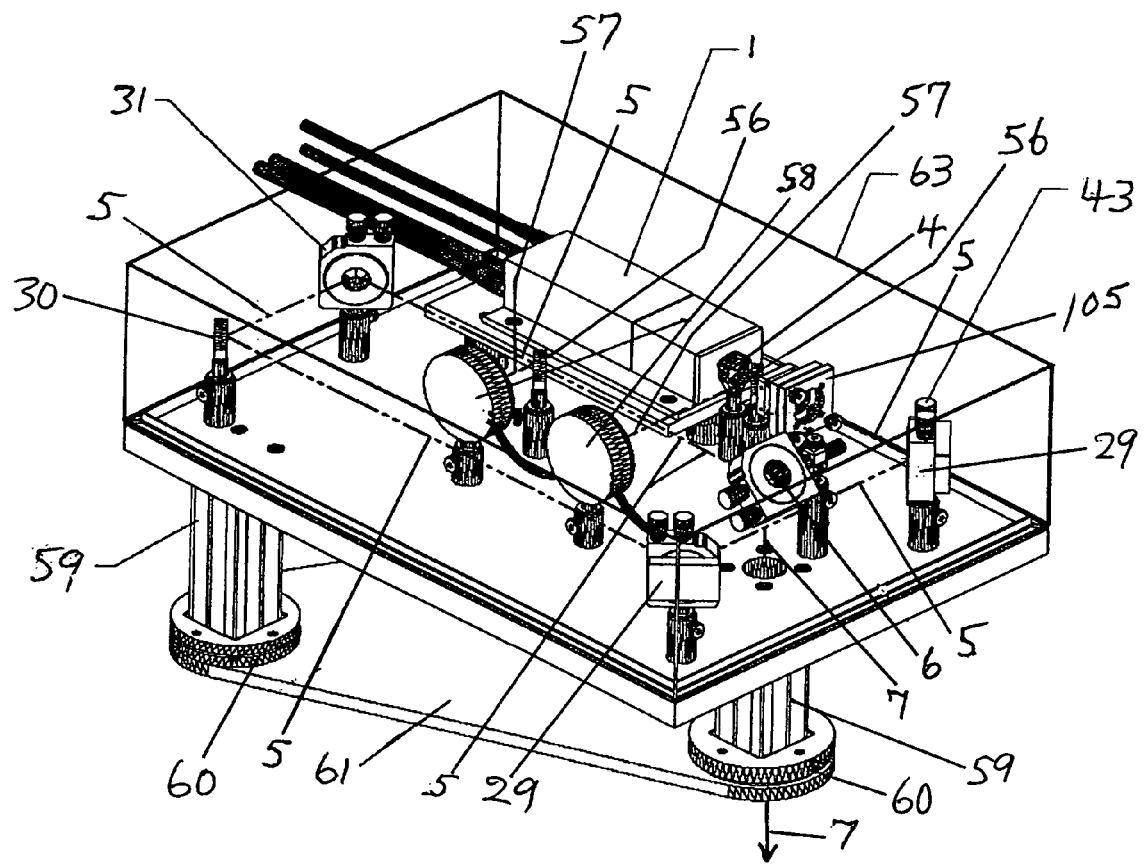
FIG. 7B is a shorter path version of FIG. 7A with fewer mirrors and 2 energy meters (58).
Figure 8A:
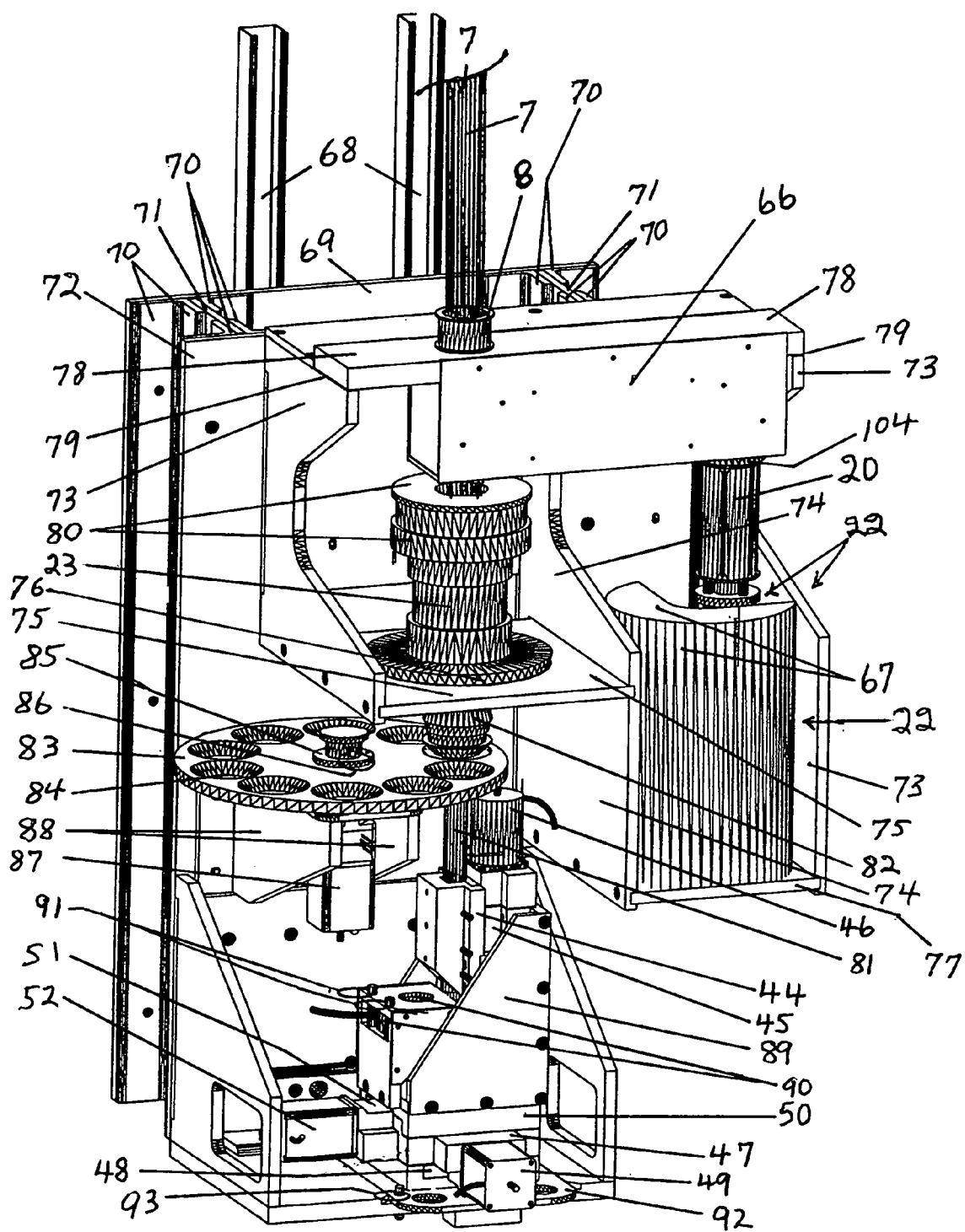
FIG. 8A is a lower module (inside radiation hot cell) of rad-hardened laser ablation invention.
Figure 8B:
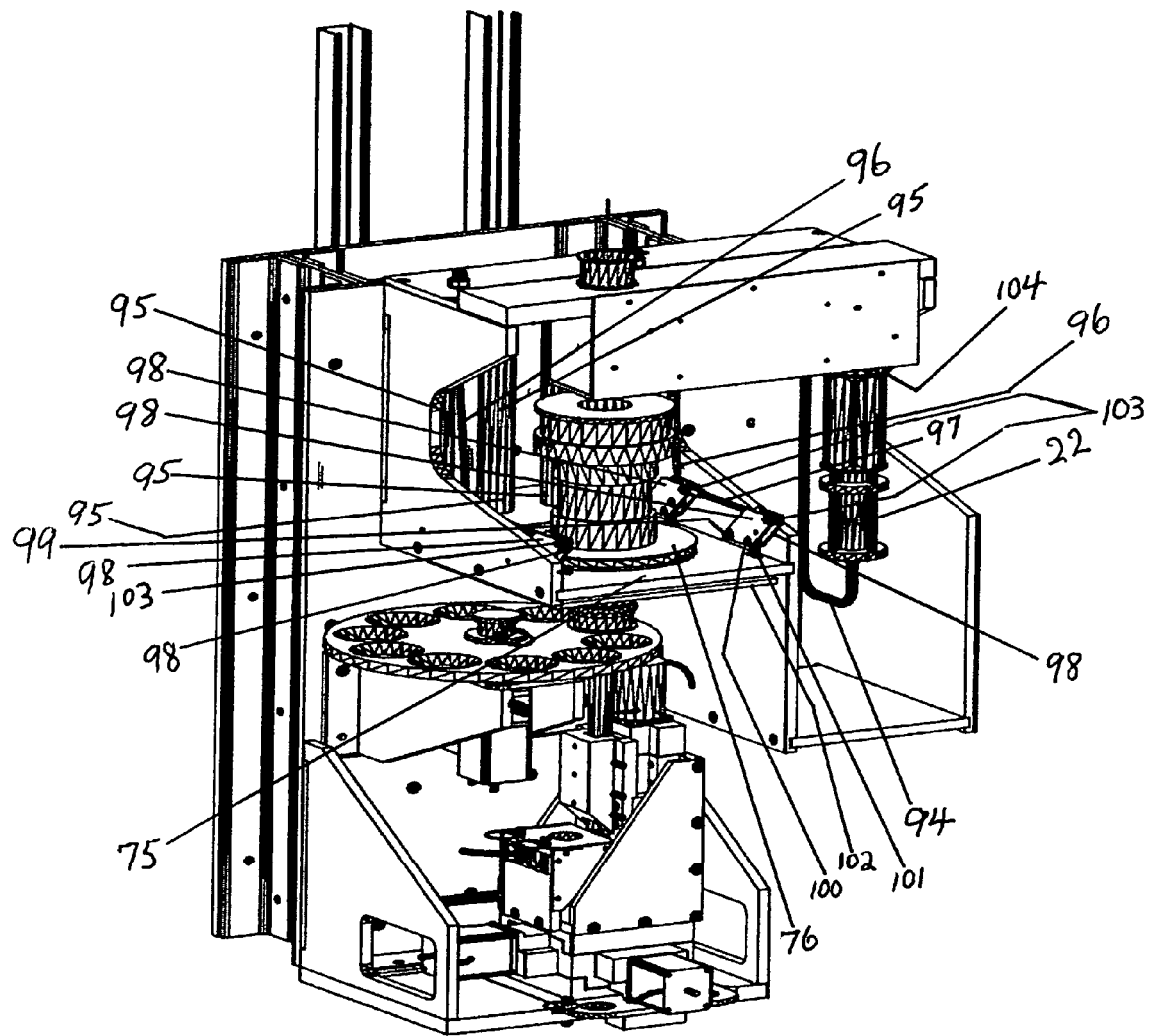
FIG. 8B is the same as 8A but with shield (67) removed, and with addition of a counterbalancing force (95) to offset weight of the ablation cell (23).
Figure 9A:
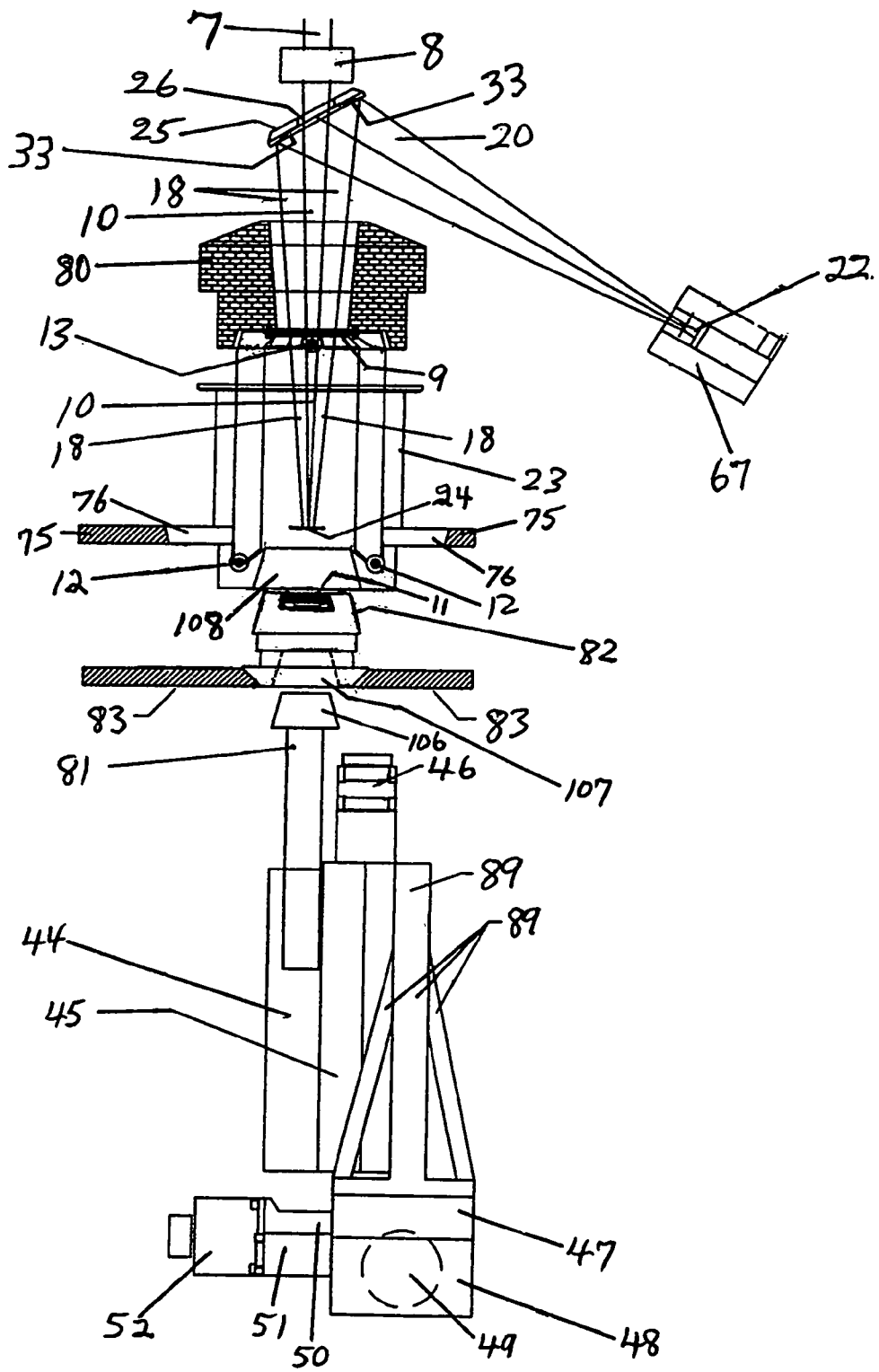
FIG. 9A. is another invention version of the FIG. 8A preferred embodiment.
Figure 9B:
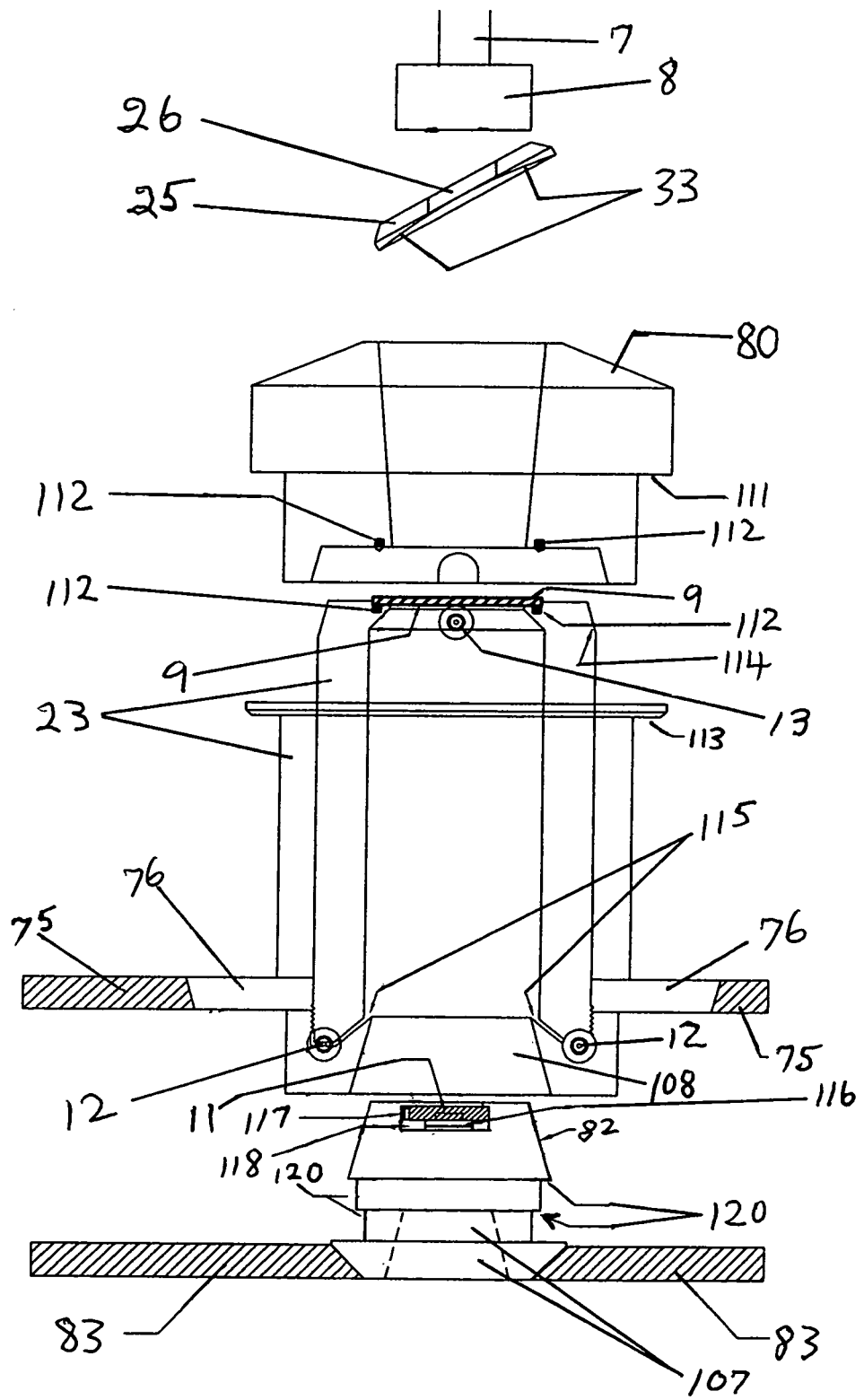
FIG. 9B. is an exploded view of a stacking ablation cell (23) from FIG. 9A.
Figure 9C:
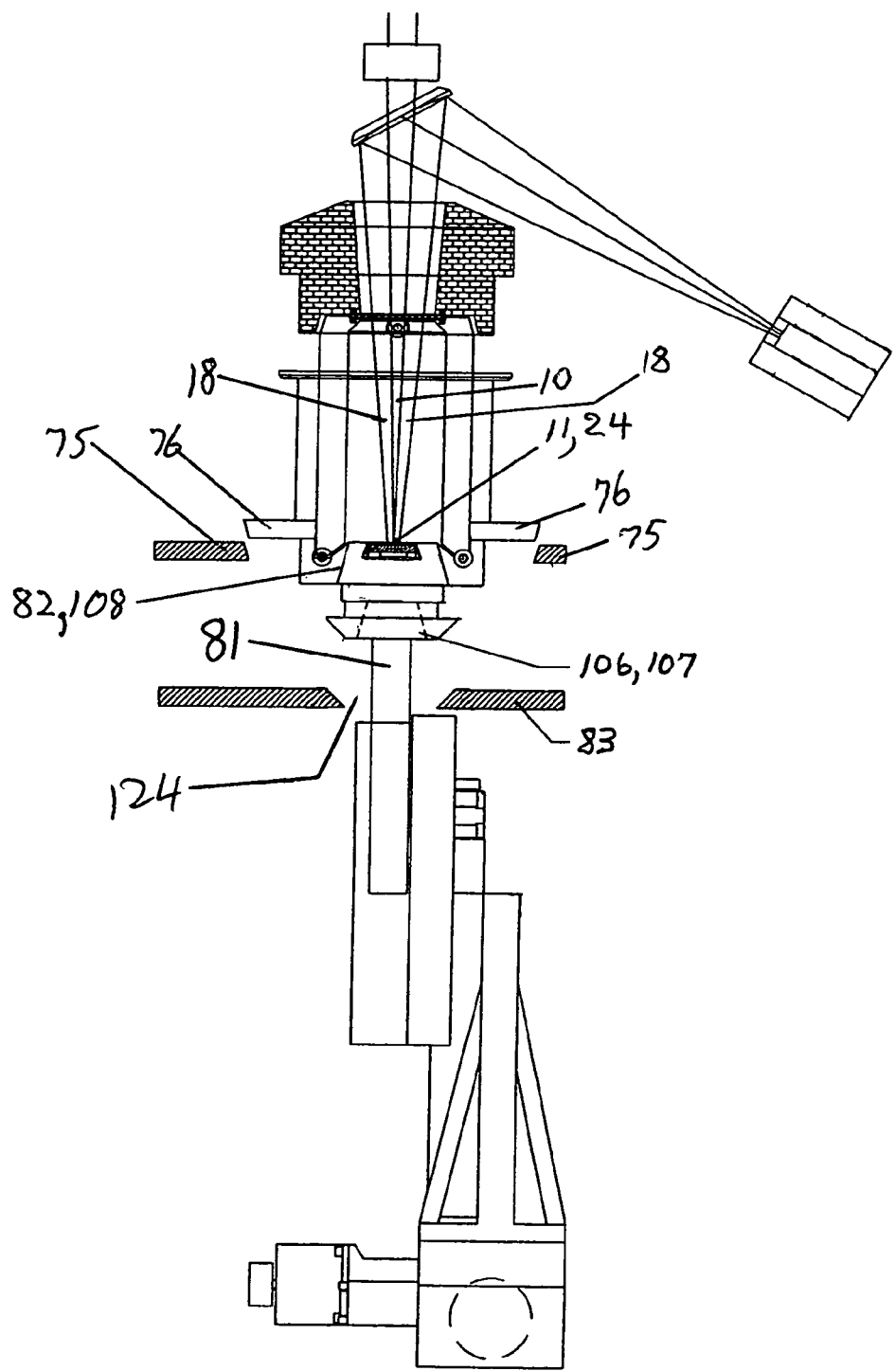
FIG. 9C shows the sample holder lifted out of its platform (83) engaging the ablation cell and lifting it out of its platform (75), focusing sample 11 at objective lens focal plane (24).
Figure 9:
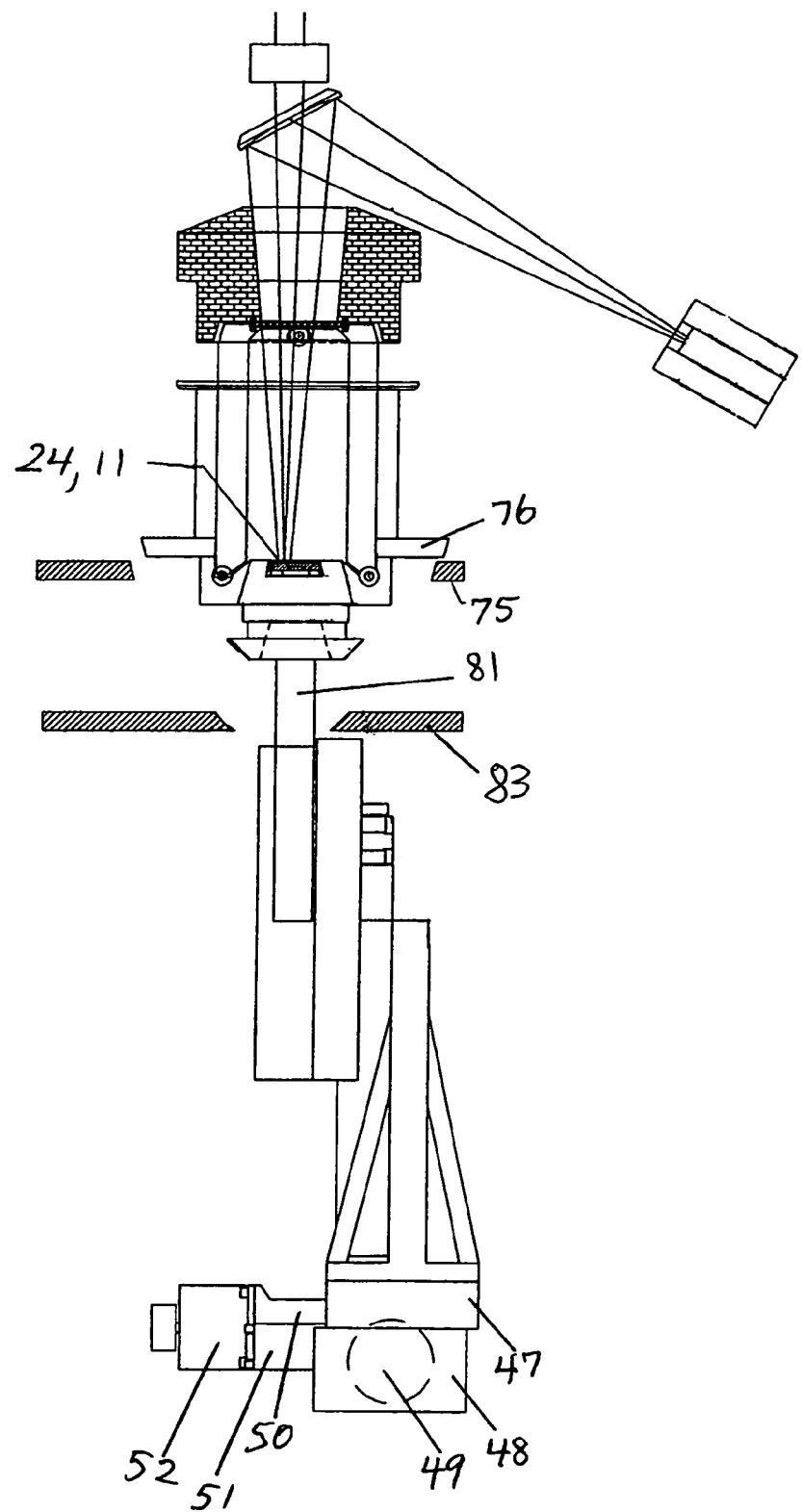
FIG. 9D is the same as 9C except platform 47 has motor scanned to the right, effecting a line scan of the laser beam to the left on sample 11, 24.

A final advantage of the "mirror-with-hole" invention laser ablation viewing system is that a conventional prior art thin-film coated dichroic mirror ((6) in FIG. 1A-B) is replaced by the invention mirror-with-hole (25, 26) at an invention optical convergence point of the two paths (see FIGS. 2A-B, FIGS. 9A-B), and eliminating the thin-film coating of a prior art dichroic mirror allows a preferred embodiment invention UV laser ablation (FIGS. 7A-B, 8A-B) to function in a radiation "hot cell" for analysis of high activity nuclear waste, if the invention laser beam (7) originates outside of the "hot cell" (see FIGS. 7A-B), and the FIG. 7A-B invention final line-of-sight mirror (6)—line of sight to a FIG. 9A (also FIG. 8A-B) radioactive solid sample (11, 24) and also the invention camera (22) are rad-hardened and/or shielded, respectively. To rad-harden invention line-of-sight mirror (6), it cannot be a conventional prior art dichroic laser mirror (subject to rapid radiation damage), and a fully aluminized invention line-of-sight mirror would have to be substituted instead. (Conventional prior art thin film dichroic mirror coatings are rapidly destroyed by radiation damage at 1,000 rads/hour exposure in an activated radiation "hot cell".) The FIG. 7A-B invention aluminized final line-of-sight laser steering mirror (6) has a reduced reflectance of about 96% R when new, compared with a new (non-irradiated) prior art dichroic mirror (99.7% R), but after a short time (e.g. within a few minutes or hours) of exposure to high activity nuclear waste (e.g. 1000 rads/hr), the prior art dichroic mirror will be destroyed, but the invention aluminized final line-of-sight steering mirror will still be 96% R. A small percentage reduction of initial reflectance in the invention line-of-sight steering mirror (6) thus extends the invention useful lifetime to about 6-12 years, rather than 6-12 minutes (or hours) lifetime for a prior art system. A preferred FIGS. 7A-B, 8A-B, FIGS. 9A-D rad-hardened embodiment of the invention analytical UV laser ablation system is thereby enabled for the analysis of solid nuclear waste (11, 24).

One preferred invention embodiment employs a split architecture invention laser ablation system for a radiation hot cell as in FIGS. 7A-B, 8A-B, in which FIGS. 7A-B invention laser, invention upper energy meters (58) and invention laser steering mirrors are located outside of the hot cell with a beam from the invention laser entering the hot cell through a window in the hot cell, and in which the FIGS. 8A-B invention "lower module" comprising an invention long focal length (uncoated) laser objective lens, mirror-with-hole, invention uncoated view camera lens, invention shielded view camera, invention ablation cell, invention automated sample changer, invention ablation cell translational motion stages (facilitating sample focus, line scan ablation, and raster pattern ablation), and invention lower energy meter (90) is located inside the hot cell, and in which said FIGS. 8A-B invention "lower module" components in the hot cell are rad-hardened and/or radiation shielded and/or exhibit placement "at greater than normal distance" from radioactive samples, to permit each said invention lower module component and the overall invention lower module to withstand at least 100,000 rads and preferably up to 100 million rads total lifetime radiation exposure prior to a radiation damage failure point, and in which additional invention laser ablation components receiving "line of sight" radiation outside the hot cell, such as a final invention laser beam steering mirror directing the external invention laser beam into the hot cell is rad-hardened to withstand radiation exposure, and in which an invention valve module, directing the flow of carrier gas and/or purge gas to and from the invention ablation cell, is a rad-hardened valve module capable of withstanding radiation exposure.

In preferred embodiments of the invention (either "cold" or rad-hardened) laser ablation system, a demountable sample ablation cell for laser ablation analysis is employed in which the ablation cell components assemble and seal by vertically stacking (mating) components, without using fasteners, tie downs, latches, clamps, snaps, bolts or any other fastener or clamping means. Assembly and sealing is simply by stacking the mated components vertically, and demounting is simply by unstacking the components (with simple "lift off" means), without need to remove or release any fastener, latch, or clamp. In a preferred embodiment invention demountable sample cell, gas seals are achieved by a weight compression factor, with upper cell components having sufficient weight to deliver a sealing force to mating lower cell components. The seals or a combination of seals are selected from among a group comprising tapered seals, gaskets, and o-rings and in which the selected seals are compressed to their gas sealing points solely by the weight of stacked overhead cell components.

If the weight of stacked overhead cell components becomes excessive, a FIG. 8B preferred embodiment of the invention employs a demountable sample cell in which a counterbalancing force (95) is applied to offset the combined weight of stacked cell (23) components without diminishing sealing forces below their gas sealing points, in order to allow "light duty" X, Y, Z translational stages to control the combined stacked cell positioning. The counterbalancing force may involve a spring loaded plate or platform, or it may involve at least one counterbalancing weight (95).

In a preferred invention embodiment, an invention sample changer for laser ablation analysis may cause samples or sample holders (containing samples) to be lifted out of a counter bore in a movable platform selected from a movable platform group comprising a rotary carousel, an R-Theta rotating/sliding tray, an X, Y sliding tray, or a linear feed-through tray or conveyor, said samples or sample holders (containing samples) being lifted out of said movable platform by a mechanized push rod which pushes upward through a through-hole (or other opening) contained within the counterbore, and lifts the samples or sample holders (containing samples) up and out of the movable platform, and in which the lifting action further places the samples or sample holders in proximity to a laser ablation sample cell.

In a preferred embodiment a segment of the push rod o.d. diameter is less than the i.d. of the through-hole (or opening) in the movable platform, to an extent which allows horizontal motion of the push rod to effect a line scan, or X,Y raster scan, or R-Theta raster scan of the sample horizontally in the laser beam. The invention sample changer's movable platform sequentially presents the samples or sample holders (containing samples) of a group "one at a time" for the push rod to sequentially lift into proximity to the laser ablation sample cell, so that each sample may be analyzed sequentially (in turn) by laser ablation analysis. In one embodiment, the sample changer lifting action seals the sample or sample holder (containing a sample) against or into a sample cell via weight stacked matching tapers (an o.d. inserting taper on the sample holder mating to an identical i.d. receiving taper in the base of the sample cell).

The sample changer may continue push rod lifting action after sealing to further lift the sample ablation cell and sample or sample holder (containing a sample) as a stack, said lift proceeding upward to lift the stack out of a stationary sample cell holding platform and further continues the lift until the upper surface of the sample reaches a laser ablation focal plane or a specified defocused laser ablation plane. The mechanized push rod and lift stage is further mounted atop an X, Y or R-Theta translational stage capable of offsetting the push rod with stacked sample holder, sample, and sample ablation cell in a limited linear horizontal motion or a limited X, Y horizontal raster pattern, or a limited arc motion or a limited R-Theta raster pattern during repetitively firing laser ablation events or to selected stationary horizontal offset positions for laser ablation after lifting and focusing.

Figure 10:
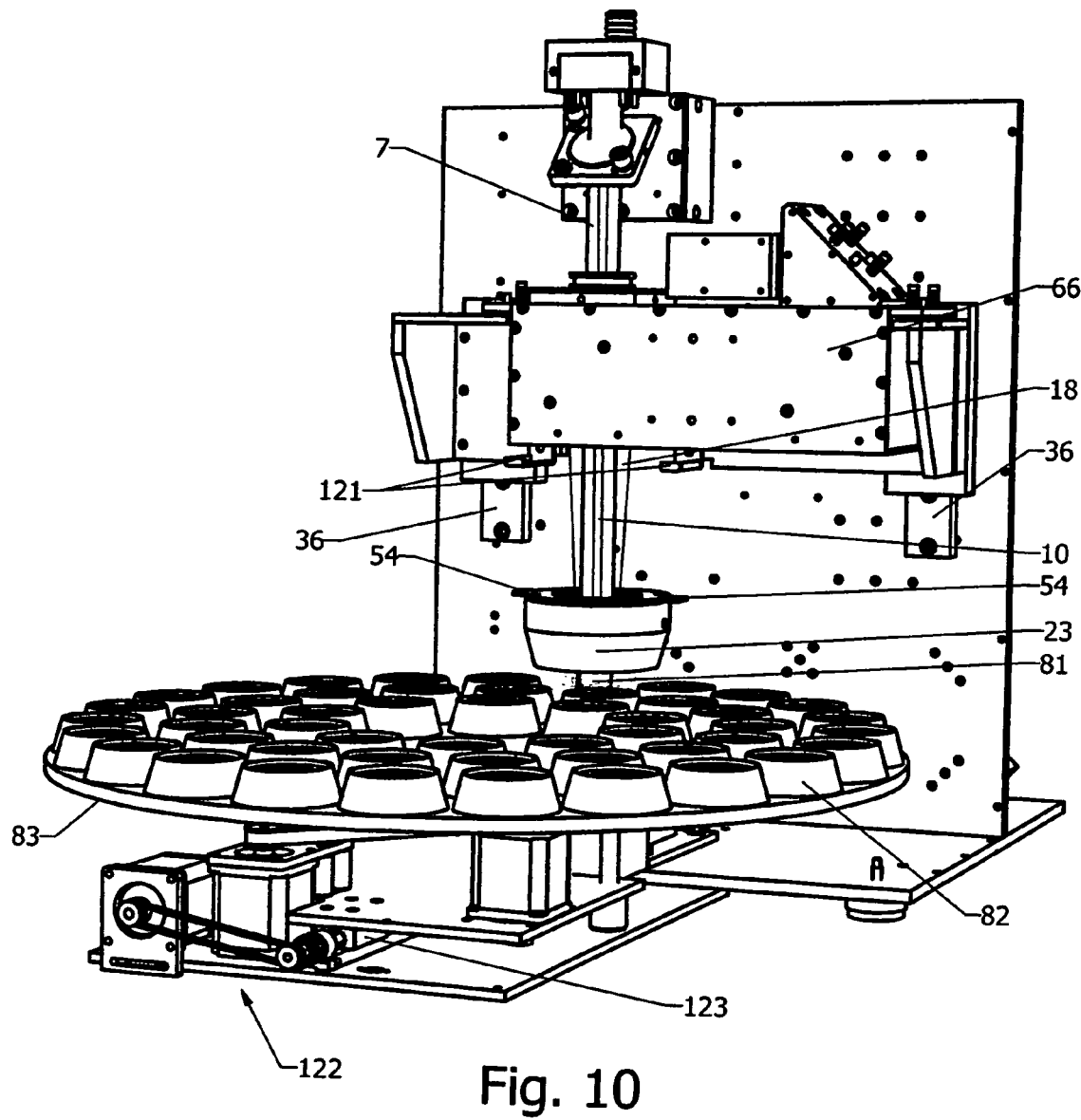
FIG. 10 illustrates a laser ablation autosampler added to a FIG. 2B laser ablation system with platter 83 lowering over stationary support rod 81 and gantry 66 having already lowered stacking ablation cell (23) onto stationary support rod (81) and tapered plug (106) (see FIG. 9A.). The FIG. 10 autosampler is an R-Theta type, in which rotary carousel 83 also translates linearly on track 123 to select among the three concentric rings containing sample holders 82.

In another FIG. 10 preferred embodiment, the invention sample changer may keep the push rod (81) vertically stationary and employ the movable platform (83) to position a sample over the push rod and then lower the sample or sample holder (82) (containing sample) onto the push rod and the platform continues to lower after the sample engages the top of the push rod, such that the platform lowers itself to clear the bottom edge of the sample or sample holder. In this embodiment it is preferred that invention laser focusing be performed by vertical rise or fall of an invention overhead gantry (66) containing at least the laser objective lens. In a preferred embodiment, the invention gantry would also support the invention visible white light viewing system and mirror-with-hole. In a preferred embodiment, the gantry also functions to raise or lower the sample ablation cell enclosure (23) over the stationary sample by means of lifting/lowering hooks (121) engaging/disengaging lift tabs (54) on the ablation cell (23).

In another embodiment, an invention sample ablation cell for laser ablation has the sample ablation cell closed on the top and open on the bottom, and in which the open bottom is positioned in proximity to a sample surface, and in which carrier gas enters the ablation cell via the annular space between the bottom of the sample ablation cell and the top of the sample surface, and in which an outer concentric "skirt" affixed to the sample ablation cell o.d. provides a compliant seal to the sample, and in which carrier gas is entered into the annular space from the skirt. In this embodiment, the sample ablation cell is horizontally stationary, but the compliant seal is a sliding seal which allows the sample to move horizontally without breaking the seal. In one embodiment, the i.d. of the bottom of the invention sample ablation cell and skirt are both smaller than the perimeter of the sample, such that the compliant seal is formed to the sample surface. In another embodiment, the i.d. of at least the skirt is larger than the perimeter of the sample, such that the compliant seal is formed to the sample holder.

In yet another alternate embodiment, the compliant seal is an inflatable and deflatable bladder which may be deflated for change of sample and inflated to re-establish perimeter seal around the sample. In this embodiment, the samples are presented sequentially in an x, y sliding tray or rotary platter, or R-theta platter during inflate/deflate cycles to effect an inexpensive automatic sample changer.

The figures and description are of nonlimiting examples, and the laser ablation invention may be envisioned beyond the scope of specific embodiments described herein, and the scope of the invention must therefore be considered to be limited only by the claims. While the invention has been described in terms of its preferred embodiments, those skilled in the art will recognize that the invention can be practiced with modification within the spirit and scope of the appended claims.

What is claimed is:

1. A target viewing system for laser ablation in which applications of the target viewing system are selected from the group consisting of laser ablation analysis of solid target samples, rad-hardened laser ablation analysis of high-activity radioactive solid target samples in a radiation hot-cell, rad-hardened laser ablation analysis of low-activity radioactive solid target samples in a radiation hot-cell, and laser micro-machining of solid target materials, and in which a target illuminator illuminates an area of interest on the target independently of the laser beam which independently ablates the target within its illuminated area of interest, and in which illumination light rays reflected from the illuminated target and viewed by the target viewing system are essentially coaxial with a final segment of the laser ablation beam immediately preceding the target, but in which the target view is not taken through any laser focusing optic, and in which the laser focus is thereby optically decoupled from the target viewing system focus, and in which the target is selected from the group consisting of a solid target sample to be analyzed by laser ablation, a high-activity radioactive solid target sample to be analyzed by rad-hardened laser ablation in a radiation hot-cell, a low-activity radioactive solid target sample to be analyzed by rad-hardened laser ablation in a radiation hot cell, and a solid target material to be micro-machined, and in which the laser ablation beam passes through an opening in an angled target viewing mirror in which the opening is selected from the group consisting of a round hole, an elliptical hole, and a slot, and in which the illumination light rays initially reflected from the illuminated target comprise the primary target view rays, and in which the target view rays are secondarily reflected toward a viewing system selected from among the group consisting of a viewing camera, a viewing projector, and a viewing eyepiece, and in which the secondary reflection of the target view rays occurs from an area of the angled target viewing mirror selected from the group of areas consisting of an area which is essentially concentric to the perimeter of the opening, an area which essentially surrounds the perimeter of the opening.

2. The target viewing system of claim 1, in which the angled target viewing mirror is located at a placement selected from the group of placements consisting of placement between a final laser focusing optic and the target, placement in which the final laser focusing optic is located at least partially within the opening in the target viewing mirror, and placement in which the final laser focusing optic protrudes at least partially through the opening in the target viewing mirror.

3. The target viewing system of claim 1 in which passing the laser beam through the opening in the angled target viewing mirror enables the angled target viewing mirror (with the opening) to replace a conventional (prior-art) dichroic laser mirror which is otherwise normally used in prior-art laser ablation to simultaneously reflect a prior-art laser ablation beam to a solid target material for purposes of ablating the solid target material while simultaneously transmitting prior-art white-light primary target-view rays from the solid target material to a prior-art view camera, and in which invention replacement of the prior-art dichroic laser mirror eliminates radiation-damage-prone prior-art dichroic laser mirrors from the invention target viewing system, and in which elimination of radiation-damage-prone prior-art dichroic laser mirrors from the invention target viewing system essentially imparts a degree of rad-hardening to the invention target viewing system, and in which the degree of rad-hardening imparted to the invention target viewing system enables it to serve as a robust target viewing system for laser ablation analysis of radioactive solid target samples in a radiation hot-cell.

4. The target viewing system of claim 3 in which an added reflector intercepts the secondarily reflected target-view rays before they reach the viewing camera, and in which the added reflector reflects the secondarily reflected target-view rays behind a radiation shield to the viewing camera which is also located behind the radiation shield, and in which at least the target viewing system, the radioactive solid target sample, the final laser focusing optic, the added reflector, the radiation shield, and the viewing camera are all located within a radiation hot-cell, and in which the target viewing system operates robustly in the radioactive environment.

5. The target viewing system of claim 4 in which at least one achromatic optical condensing element focuses the secondarily reflected target-view rays to form an image of the solid target sample onto the viewing camera.

6. The target viewing system of claim 1 in which a surface contour of the angled target viewing mirror (with opening) is selected from the group consisting of a flat, a toroid, and a curved mirror.

7. Variable demagnification laser ablation system in which the laser ablation system applications are selected from the group consisting of laser ablation analysis of solid samples and laser micro-machining of solid materials, and in which the variable demagnification laser ablation system comprises a laser, at least two beam-steering laser mirrors, and a laser-focusing objective optic, and in which a focused beam of the laser produced by the laser-focusing objective optic removes (by ablation at focused laser beam irradiance exceeding a surface damage threshold of a solid target in which the solid target is selected from the group consisting of a solid sample to be analyzed by laser ablation and a solid material to undergo laser micro-machining, and in which laser ablation occurs within a laser spot of the focused laser beam impinging on the solid target placed in proximity to an image plane of the laser spot produced by the laser-focusing objective optic, and in which micro-machining occurs within a laser spot of the focused laser beam impinging on the solid target placed in proximity to an image plane of the laser spot produced by the laser-focusing objective optic) a portion from the surface of the solid target, for purposes selected from the group consisting of altering the shape of the solid target, altering the topography of the solid target, and obtaining a plume in which the plume is selected from at least one among the group consisting of a plume of vapors, a plume of smoke, and a plume of particulate aerosol from a laser ablation event occurring on the surface of the solid target, and in which the plume may injected into a flowing carrier gas stream leading from the solid target contained within an ablation cell to an external analytical instrument selected from among the group of external analytical instruments consisting of an inductively coupled plasma (ICP) emission spectrometer, an inductively coupled plasma mass spectrometer (ICP-MS), and a flowing after-glow (FAG) mass spectrometer (FAG-MS), and in which the external analytical instrument is capable of providing analysis of the plume, in which the analysis is selected from a group consisting of chemical analysis and elemental analysis, and in which the analysis of the plume is representative of the composition of the original solid target, and in which changes in the extent of optical demagnification of the laser spot used to ablate the target may be made on an operational basis for purposes of altering the focused laser beam irradiance of the laser spot impinging on the solid target to optimize parameters selected from the group consisting of target ablation rate, aerosol quality, aerosol particle size, target ablation crater size, target ablation crater quality, target ablation trench size, and target ablation trench quality within the ideal irradiance range (IIR) of each solid target, for at least two different solid targets exhibiting at least two different ideal irradiance ranges, and in which the extent of optical demagnification of the laser spot is nominally determined as a demagnification ratio $L_1/L_2$ of a first laser optical path length ($L_1$) to a second laser optical path length ($L_2$), in which the first laser optical path length ($L_1$) is the length of a first segment of the laser beam occurring between a region proximal to the laser head and a region proximal to the laser-focusing objective optic, and in which the second laser optical path length ($L_2$) is the length of a second segment of the laser beam occurring between the laser-focusing objective optic and the solid target placed in proximity to an image plane (IP) of the laser-focusing objective optic, and in which a lens formula is essentially obeyed ($1/IP+1/L_1=1/F$), where F is the effective focal length of the laser-focusing objective optic), and in which variation in the extent of optical demagnification of the laser spot is achieved by altering the first laser optical path length ($L_1$), and in which altering the first laser optical path length ($L_1$) produces a shift in the location of the image plane (IP) of the laser spot plus a corresponding alteration of the length of the second laser optical path ($L_2$) according to the lens formula, and in which the solid target is relocated proximal to the shifted image plane IP of the laser spot, and in which the altered extent of optical demagnification of the laser spot is nominally determined as the new ratio of the altered first laser optical path length ($L_1$) to the altered second laser optical path length ($L_2$), and in which at least two different first laser optical path lengths ($L_1$) are selectable in the same laser ablation system thereby creating a choice of at least two different demagnification ratios ($L_1/L_2$), and in which selection between the at least two different first laser optical path lengths is made by a unidirectional equidistant translational offset of the positions of the at least two beam-steering laser mirrors, and in which the unidirectional equidistant translational offset is selected from the group of offsets consisting of a longitudinal offset parallel to the incident laser beam and a lateral offset perpendicular to the incident laser beam, and in which the at least two beam-steering laser mirrors are placed in a segment of the laser beam corresponding to the first laser optical path, and in which the unidirectional equidistant translational offset of the positions of the at least two beam-steering laser mirrors occurs within the segment of the laser beam corresponding to the first laser optical path essentially altering the first laser optical path length $L_1$.

8. The variable demagnification laser ablation system of claim 7 in which, for the case of the longitudinal offset (parallel to the incident laser beam), a first beam-steering laser mirror of the at least two beam-steering laser mirrors is angled at essentially 45 degrees (e.g., 45 degrees clockwise, in a nonlimiting example) to a portion of the laser beam incident on the first beam-steering laser mirror thereby producing essentially a 90 degree primary reflection (e.g., 90 degrees clockwise, in a nonlimiting example) of the laser beam, and in which a second beam-steering laser mirror of the at least two beam-steering laser mirrors is positioned to receive the beam reflected from the first beam steering laser mirror, and in which the second beam-steering laser mirror is angled at essentially 45 degrees (e.g., 45 degrees clockwise, in a nonlimiting example) to the 90 degree primary reflected laser beam thereby producing an additional 90 degree secondary reflection (e.g., an additional 90 degrees clockwise, in a nonlimiting example) of the laser beam, and in which the secondarily reflected laser beam is traveling essentially parallel to the incident beam (but in the opposite direction), and in which the optical path traced by the incident portion of the laser beam, the segment of the laser beam immediately following primary 90 degree reflection, and the segment of the laser beam immediately following secondary 90 degree reflection essentially traces the shape of a rectangular box with only three sides showing, and in which the simultaneous unidirectional equidistant translational offset of the positions of the at least two beam-steering laser mirrors used to alter the first laser optical path length ($L_1$) occurs essentially parallel to the incident portion of the laser beam and in a direction selected from among a group of directions consisting of directly toward the incident beam origin (thereby shortening the first laser optical path length ($L_1$) by an amount essentially twice the offset) and directly away from the incident beam origin (thereby lengthening the first laser optical path length ($L_1$) by an amount essentially twice the offset, and in which the segment of the laser beam immediately following secondary 90 degree reflection after altering the first laser optical path length remains coincident with its original path (before altering the first laser optical path length ($L_1$)).

9. The variable demagnification laser ablation system of claim 8, in which the at least two beam-steering laser mirrors are mounted on a common base, and in which the common base may be relocated to produce the simultaneous unidirectional equidistant longitudinal translational offset of the positions of the at least two beam-steering laser mirrors within the segment of the laser beam corresponding to the first laser optical path.

10. The variable demagnification laser ablation system of claim 9, in which an optical mount of at least one of the at least two beam-steering laser mirrors is an adjustable gimbaling mount, and in which the common base relocation to produce the simultaneous unidirectional equidistant longitudinal translational offset of the positions of the at least two beam-steering laser mirrors is accompanied by at least one readjustment of the at least one adjustable gimbaling mount to correct for any overall laser beam misalignment which may have occurred as a result of the common base relocation and accompanying translational offset, and in which the at least one readjustment restores laser beam alignment of the first laser optical path segment after common base relocation to a condition of coincidence with overall laser beam alignment before common base relocation.

11. The variable demagnification laser ablation system of claim 10, in which the at least one readjustment of the at least one adjustable gimbaling mount is performed using a method selected from the group of methods consisting of manual readjustment based on restoring the focused laser spot position to a predetermined reference target position, manual readjustment to a predetermined precision readjustment setting which has been predetermined to consistently restore the focused laser spot position to a predetermined reference target position, and automated readjustment by a computer algorithm controlling a precision stepper motor which performs motorized readjustment to a predetermined precision readjustment setting which has been predetermined to consistently restore the focused laser spot position to a predetermined reference target position.

12. The variable demagnification laser ablation system of claim 9, in which the common base supporting the at least two laser mirrors comprises a first base sub-assembly, and in which at least a second common base supporting at least two additional laser mirrors comprises a second base sub-assembly, and in which the first base sub-assembly is kinematically mounted to a fixed laser ablation platform in a first position, and in which the second base sub-assembly is kinematically mounted to the fixed laser ablation platform in a second position which is offset from the first position, and in which the first base sub-assembly can be removed from its kinematic mount and replaced to its kinematic mount without need of realignment of its laser mirrors such that original laser alignment is maintained and reproduced upon first sub-assembly replacement to its first kinematic mount receiver, and in which the second base sub-assembly can be removed from its second kinematic mount and replaced to its second kinematic mount without need of realignment of its additional laser mirrors such that original laser alignment is maintained and reproduced upon second sub-assembly replacement to its second kinematic mount receiver, in a manner and in which only one of the at least two common bases is installed at a time, and in selection between which of the at least two common bases is installed at any given time will determine which of the corresponding at least two different laser spot demagnification ratios will be selected, and in which selection between the at least two different laser spot demagnification ratios is achieved simply by selecting which of the at least two common bases to install in their respective locations, and in which installing a new common base does not require mirror realignment, and in which installing a new common base produces the same effect as relocation of a single common base to produce the simultaneous unidirectional equidistant translational offset of the positions of the at least two beam-steering laser mirrors to produce a desired change of laser spot demagnification.

13. The variable demagnification laser ablation system of claim 7 in which, for the case of the lateral offset (perpendicular to the incident laser beam), at least two more beam steering mirrors are added to create a set of at least four beam steering mirrors which yield path-lengthening, four-step optical detour for the incident laser beam, and in which the four-step optical detour initially leads the reflected laser beam essentially perpendicularly away from the incident laser beam path in a primary reflection by the first laser beam steering mirror of the at least four laser beam steering mirrors, eventually turning the laser beam essentially parallel again to the incident laser beam path (proceeding in the same direction as the incident laser beam (but with an offset)) in a secondary reflection by the second beam steering laser mirror of the at least four beam steering laser mirrors, and then turning the laser beam essentially perpendicularly toward the incident laser beam path in a tertiary reflection by the third laser beam steering mirror of the at least four laser beam steering mirrors, and finally turning the laser beam essentially perpendicularly again in a quaternary reflection by the fourth laser beam steering mirror of the at least four laser beam steering mirrors, and in which the laser beam (following quaternary reflection) is on a path which is essentially coaxial (without offset) with a path which the incident laser beam would have followed if the four step optical detour had not occurred, and in which the alteration of path length $L_1$ introduced by the four-step optical detour is essentially twice the distance between the first and second laser beam steering mirrors of the at least four laser beam steering mirrors.

14. The variable demagnification laser ablation system of claim 13 in which the second and third laser beam steering mirrors are maintained in a fixed position while the first and fourth laser beam steering mirrors of the at least four laser beam steering mirrors may be mechanically positioned on an operational basis to a location selected from the group of locations consisting of in the laser beam or removed from the laser beam, and in which the location in the laser beam enables the four step path-lengthening optical detour, and in which the location removed from the laser beam eliminates the four step path-lengthening optical detour such that choice of two different $L_1$ path lengths is offered by selecting location of the first and fourth laser beams steering mirrors of the at least four laser beam steering mirrors to be either in the laser beam or removed from the laser beam.

15. The variable demagnification laser ablation system of claim 14 in which the first and fourth laser beam steering mirrors are mounted on a movable platform which inserts them into the laser beam enabling the four-step optical detour when the platform is moved in one direction perpendicular to the incident laser beam, and in which the first and fourth laser beam steering mirrors are removed from the laser beam disabling the four-step optical detour when the platform is moved in the opposite direction, and in which the movable platform contains at least one additional pair of laser beam steering mirrors oriented at the same angles as the first and fourth laser beam steering mirrors but with a different spacing between them than is exhibited by the first and fourth laser beam steering mirrors, and in which the at least one additional pair of laser beam steering mirrors is offset in the direction of the four stage optical detour path, and in which the extent of relocation of the movable platform determines whether the first and fourth laser beam steering mirrors are inserted into the laser beam or whether the at least one additional pair of laser beam steering mirrors is inserted into the laser beam, and in which insertion of the first and fourth laser beam steering mirror pair enables a first optical detour path length based on the first, second, third, and fourth laser beam steering mirrors, and in which insertion of the at least one additional pair of laser beam steering mirrors enables a second optical detour path length based on the at least one additional pair of laser beam steering mirrors plus at least a second additional pair of laser beam steering mirrors which have a different optical detour path offset from the laser beam than the second and third laser beam steering mirrors of the at least four laser beams steering mirrors and in which the at least a second additional pair of laser beam steering mirrors has a spacing between the two laser beam steering mirrors of the at least a second pair of additional beam steering mirrors equivalent to the spacing between the two laser beam steering mirrors of the at least one additional pair of laser beam steering mirrors, and in which the extent of relocation of the movable platform determines the optical path length to be selected from among the group of optical path lengths consisting of at least the first optical detour path, the second optical detour path, and no optical detour.

16. The variable demagnification laser ablation system of claim 15 in which at least the first optical detour path and the second optical detour path are nested, one within the other.

17. The variable demagnification laser ablation system of claim 15 in which at least the first laser beam steering mirror of the at least four laser beam steering mirrors and the first-encountered laser beam steering mirror of the at least one additional pair of laser beam steering mirrors are combined into a single larger mirror, and in which at least the fourth laser beam steering mirror of the at least four laser beam steering mirrors and the second laser beam steering mirror of the at least one additional pair of laser beam steering mirrors are combined into a single larger mirror, and in which relocation of the movable platform within the laser beam selects at least two different portions of the combined first-encountered single larger mirror (combined from the first laser beam steering mirror of the at least four laser beam steering mirrors and the first-encountered laser beam steering mirror of the at least one additional pair of laser beam steering mirrors) and at least two different portions of the combined second-encountered single larger mirror (combined from the fourth laser beam steering mirror of the at least four laser beam steering mirrors and the second-encountered laser beam steering mirror of the at least one additional pair of laser beam steering mirrors).

18. A long focus laser ablation system in which the laser ablation system applications are selected from the group consisting of laser ablation analysis of solid samples and laser micro-machining of solid materials, and in which the long focus laser ablation system comprises a laser, at least two beam-steering laser mirrors, and a laser-focusing objective optic, and in which a focused beam of the laser produced by the laser-focusing objective optic removes (by ablation at focused laser beam irradiance exceeding a surface damage threshold of a solid target in which the solid target is selected from the group consisting of a solid sample to be analyzed by laser ablation and a solid material to undergo laser micro-machining, and in which laser ablation occurs within a laser spot of the focused laser beam impinging on the solid target placed in proximity to an image plane of the laser spot produced by the laser-focusing objective optic, and in which micro-machining occurs within a laser spot of the focused laser beam impinging on the solid target placed in proximity to an image plane of the laser spot produced by the laser-focusing objective optic) a portion from the surface of the solid target, for purposes selected from the group consisting of altering the shape of the solid target, altering the topography of the solid target, and obtaining a plume in which the plume is selected from at least one among the group consisting of a plume of vapors, a plume of smoke, and a plume of particulate aerosol from a laser ablation event occurring on the surface of the solid target, and in which the plume may injected into a flowing carrier gas stream leading from the solid target contained within an ablation cell to an external analytical instrument selected from among the group of external analytical instruments consisting of an inductively coupled plasma (ICP) emission spectrometer, an inductively coupled plasma mass spectrometer (ICP-MS), and a flowing after-glow (FAG) mass spectrometer (FAG-MS), and in which the external analytical instrument is capable of providing analysis of the plume, in which the analysis is selected from a group consisting of chemical analysis and elemental analysis, and in which the analysis of the plume is representative of the composition of the original solid target, and in which the laser is selected from the group consisting of a pulsed ultraviolet laser, a stable multimode resonator (SMR) configured pulsed laser, a picosecond laser, and a femtosecond laser, and in which the laser focusing objective optic exhibits a focal length of at least 40 mm, and in which the focal length is sufficient to create an increased working distance between the laser focusing objective optic and a target focal plane of the laser focusing objective optic.

19. The long focus laser ablation system of claim 18 in which the working distance is sufficient to allow room for an angled target viewing mirror, in which the angled target viewing mirror has an opening through which a focused laser ablation beam from the final laser focusing optic may pass, and in which the working distance is sufficient to allow additional room for a target sample ablation chamber beneath the angled target viewing mirror.

20. The long focus laser ablation system of claim 18, in which an optical characteristic of a laser spot proximal to the target focal plane is a depth-of-focus of at least 0.4 mm, and in which the at least 0.4 mm depth of focus enables consistent ablation rates of a target under conditions of irregular target surface topography so long as the degree of irregularity in target surface topography doesn't exceed the depth of focus, and in which the degree to which a mounted target surface is parallel to a translational stage motion may be relaxed to an extent limited by the depth of focus and the unidirectional length of a trench being ablated into the target by repetitive, spatially overlapping, pulsed laser ablation event firings occurring during simultaneous translational stage motion which translates a sample ablation cell containing the target.

* * * * *